United States Patent
Hancock et al.

(10) Patent No.: US 6,702,802 B1
(45) Date of Patent: Mar. 9, 2004

(54) CATHETERS WITH IMPROVED TRANSITION

(75) Inventors: David Hancock, San Francisco, CA (US); David Chi, Santa Clara, CA (US); Michael S. Mirizzi, San Jose, CA (US); Peter S. Brown, Palo Alto, CA (US); Christopher C. Pfaff, Palo Alto, CA (US); Brett W. Cryer, Sunnyvale, CA (US); Misty L. Pyatt, Oceanside, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 489 days.

(21) Appl. No.: 09/596,014

(22) Filed: Jun. 15, 2000

Related U.S. Application Data

(60) Provisional application No. 60/164,600, filed on Nov. 10, 1999.

(51) Int. Cl.[7] .............................................. A61M 25/00
(52) U.S. Cl. ...................... 604/524; 604/524; 604/525; 604/264; 604/104; 623/1.11; 623/1.13
(58) Field of Search ................... 604/523, 524, 604/525, 264, 104; 623/1.11, 1.13, 1.15

(56) References Cited

U.S. PATENT DOCUMENTS

| | | | |
|---|---|---|---|
| 4,563,181 A | 1/1986 | Wijayarathna et al. | 604/280 |
| 4,616,652 A | 10/1986 | Simpson | 128/344 |
| 4,733,665 A * | 3/1988 | Palmaz | 128/343 |
| 4,739,768 A * | 4/1988 | Engleson | 128/658 |
| 4,782,834 A | 11/1988 | Maguire et al. | 128/344 |
| 4,790,315 A | 12/1988 | Mueller, Jr. et al. | 128/344 |
| 4,819,751 A | 4/1989 | Shimada et al. | 128/344 |
| 4,863,442 A | 9/1989 | DeMello et al. | 604/282 |
| 4,917,666 A | 4/1990 | Solar et al. | 604/95 |
| 4,976,690 A * | 12/1990 | Solar et al. | 604/96 |
| 4,994,018 A | 2/1991 | Saper | 600/18 |
| 4,998,917 A | 3/1991 | Gaiser et al. | 604/96 |
| 5,041,125 A | 8/1991 | Montano, Jr. | 606/192 |
| 5,047,045 A | 9/1991 | Arney et al. | |
| 5,078,727 A | 1/1992 | Hannam et al. | 606/194 |
| 5,087,244 A | 2/1992 | Wolinsky et al. | 604/53 |
| 5,095,915 A | 3/1992 | Engelson | 128/772 |
| 5,100,381 A | 3/1992 | Burns | 604/96 |
| 5,100,385 A | 3/1992 | Bromander | 604/99 |
| 5,158,548 A * | 10/1992 | Lau et al. | 604/96 |
| 5,171,297 A | 12/1992 | Barlow et al. | 604/96 |
| 5,304,134 A | 4/1994 | Kraus et al. | 604/96 |
| 5,308,342 A * | 5/1994 | Sepetka et al. | 604/282 |
| 5,328,468 A | 7/1994 | Kaneko et al. | 604/96 |
| 5,425,712 A | 6/1995 | Goodin | 604/96 |
| 5,439,445 A | 8/1995 | Kontos | 604/96 |
| 5,470,322 A * | 11/1995 | Horzewski et al. | 604/280 |
| 5,480,383 A | 1/1996 | Bagaoisan et al. | |
| 5,499,973 A * | 3/1996 | Saab | 604/96 |
| 5,522,800 A | 6/1996 | Crocker | 604/96 |
| 5,549,552 A | 8/1996 | Peters et al. | 604/96 |

(List continued on next page.)

Primary Examiner—Ira S. Lazarus
Assistant Examiner—Camtu Nguyen
(74) Attorney, Agent, or Firm—Fulwider Patton Lee & Utecht, LLP

(57) ABSTRACT

The present invention is directed to a balloon catheter, such as a dilatation catheter and a stent delivery catheter with improved stiffness transition and specifically with no sudden changes in stiffness along the catheter length. The balloon catheters of the present invention may be used alone or be mounted with a stent in. The balloon catheters of the present invention may be used in peripheral, coronary, or neurovascular applications. The present catheter has more than one portion with different bending stiffness values, each portion comprising of components that gradually transition the bending stiffness of that portion to an adjacent portion, thus reducing the differential in bending stiffness in moving from one region to another, when the catheter is used alone or in combination with a stent in a stent delivery system.

33 Claims, 18 Drawing Sheets

U.S. PATENT DOCUMENTS

| | | | |
|---|---|---|---|
| 5,599,319 A | 2/1997 | Stevens | 604/264 |
| 5,634,928 A | 6/1997 | Fischell et al. | 606/108 |
| 5,643,209 A | 7/1997 | Fugoso et al. | 604/96 |
| 5,653,691 A | 8/1997 | Rupp et al. | |
| 5,667,521 A | 9/1997 | Keown | 606/194 |
| 5,697,906 A | 12/1997 | Ariola et al. | 604/96 |
| 5,728,065 A * | 3/1998 | Follmer et al. | 604/96 |
| 5,728,067 A | 3/1998 | Enger | 604/102 |
| 5,746,701 A | 5/1998 | Noone | 600/585 |
| 5,749,848 A * | 5/1998 | Jang et al. | 604/53 |
| 5,759,172 A | 6/1998 | Weber et al. | 604/96 |
| 5,759,173 A | 6/1998 | Preissman et al. | 604/96 |
| 5,759,174 A | 6/1998 | Fischell et al. | 604/96 |
| 5,759,191 A | 6/1998 | Barbere | 606/194 |
| 5,762,637 A | 6/1998 | Berg et al. | 604/264 |
| 5,769,819 A | 6/1998 | Schwab et al. | 604/103 |
| 5,772,641 A | 6/1998 | Wilson | 604/280 |
| 5,776,141 A | 7/1998 | Klein et al. | |
| 5,779,731 A | 7/1998 | Leavitt | |
| 5,811,043 A | 9/1998 | Horrigan et al. | 264/138 |
| 5,823,995 A | 10/1998 | Fitzmaurice et al. | 604/96 |
| 5,826,588 A | 10/1998 | Forman | 128/898 |
| 5,836,965 A | 11/1998 | Jendersee et al. | 606/198 |
| 5,843,032 A | 12/1998 | Kastenhofer | 604/96 |
| 5,843,090 A | 12/1998 | Schuetz | 606/108 |
| 5,846,246 A | 12/1998 | Dirks et al. | 606/108 |
| 5,860,963 A | 1/1999 | Azam et al. | 604/280 |
| 5,891,110 A | 4/1999 | Larson et al. | 604/280 |
| 5,899,882 A | 5/1999 | Waksman et al. | 604/96 |
| 5,911,715 A | 6/1999 | Berg et al. | 604/525 |
| 5,944,726 A | 8/1999 | Blaeser et al. | |
| 5,968,069 A | 10/1999 | Dusbabek et al. | |
| 5,971,990 A | 10/1999 | Venturelli | |
| 6,007,543 A | 12/1999 | Ellis et al. | |
| 6,027,510 A | 2/2000 | Alt | |
| 6,077,273 A | 6/2000 | Euteneuer et al. | |
| 6,223,558 B1 | 5/2001 | Yi | |
| 6,315,790 B1 | 11/2001 | Gerberding et al. | |
| 6,322,534 B1 * | 11/2001 | Shkolnik | 604/96.01 |
| 6,325,779 B1 | 12/2001 | Zedler | |
| 6,355,027 B1 | 3/2002 | Le et al. | |
| 6,391,032 B2 | 5/2002 | Blaeser et al. | |

* cited by examiner

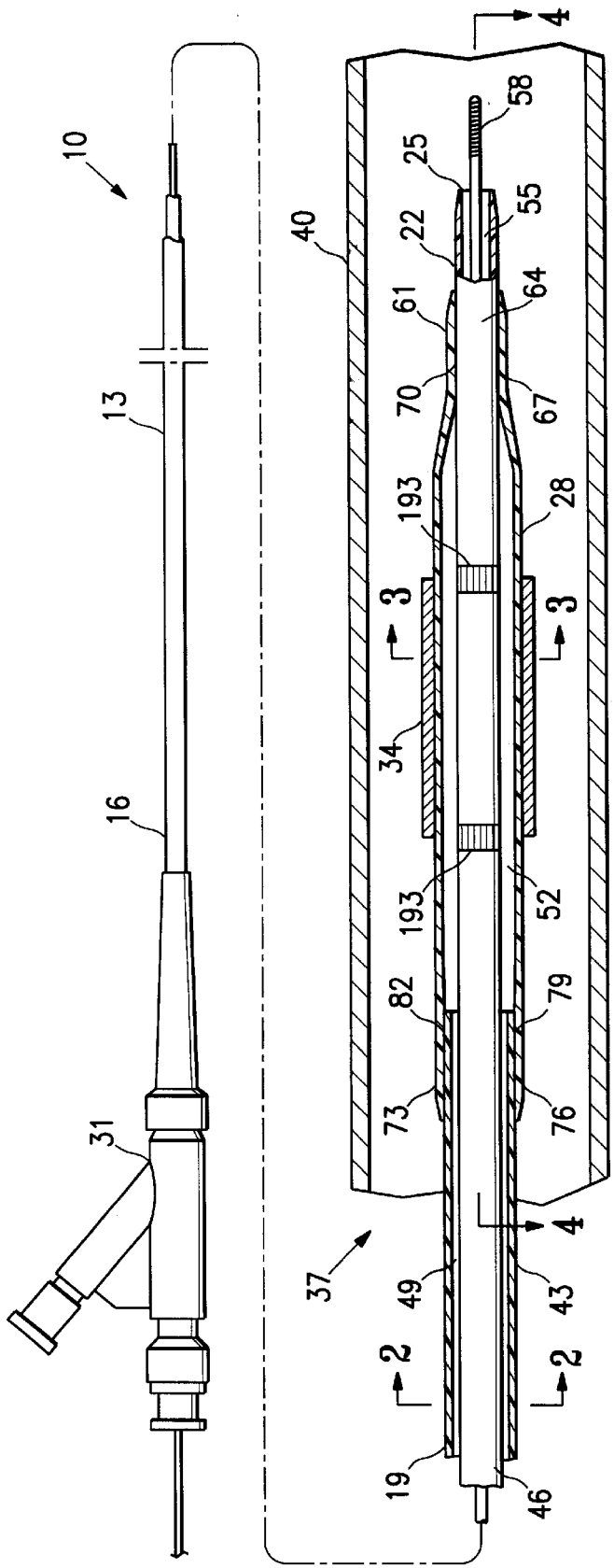
FIG. 1
FIG. 2
FIG. 3

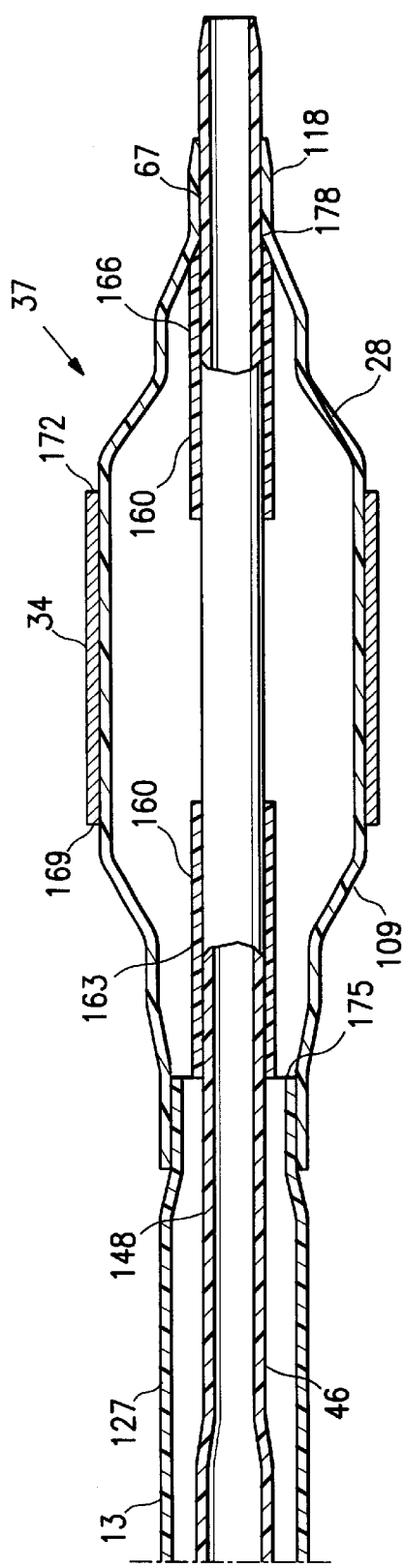
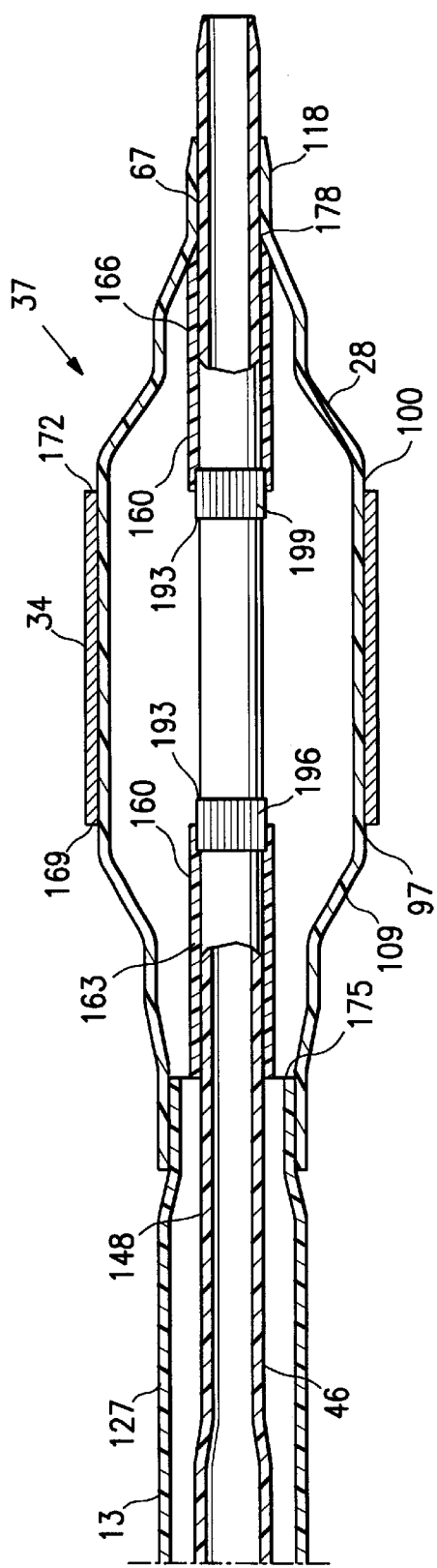
FIG. 6A
FIG. 6B

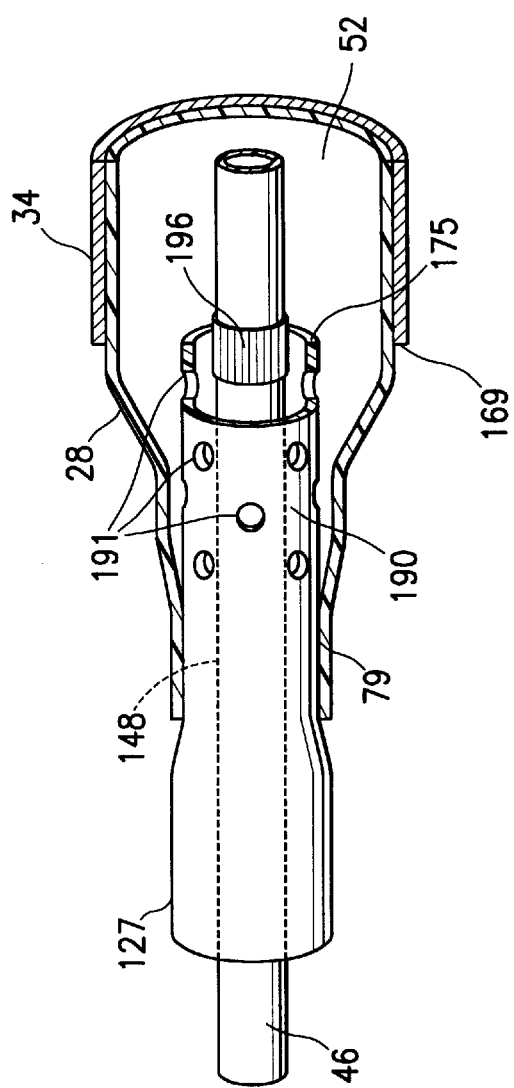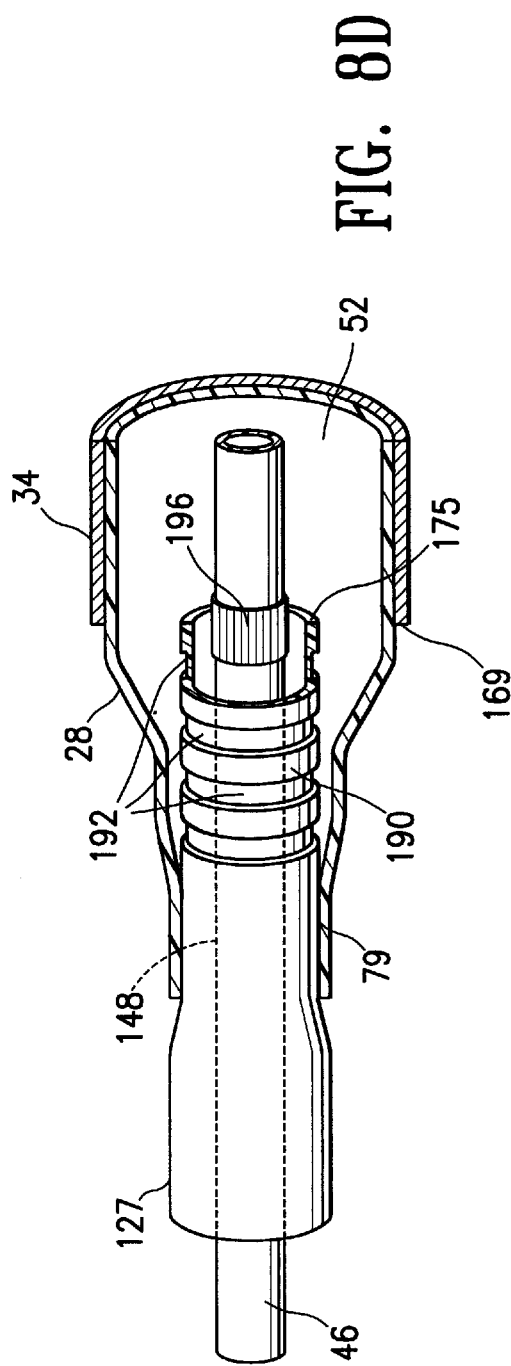

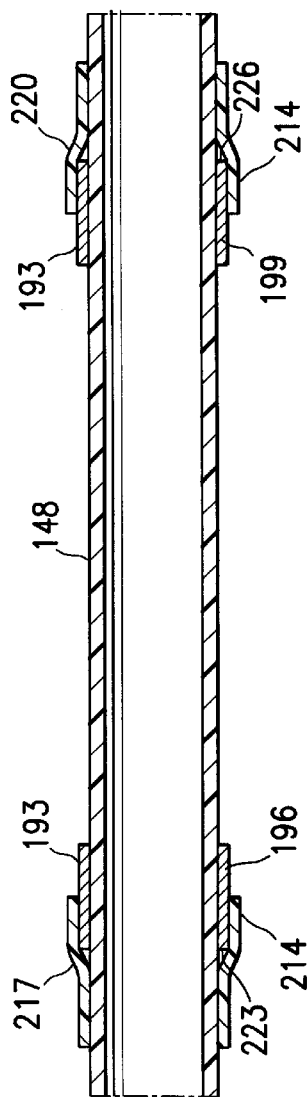
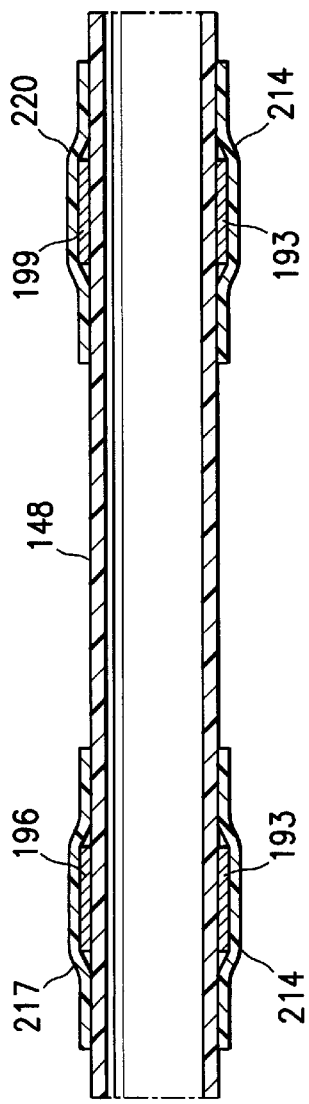
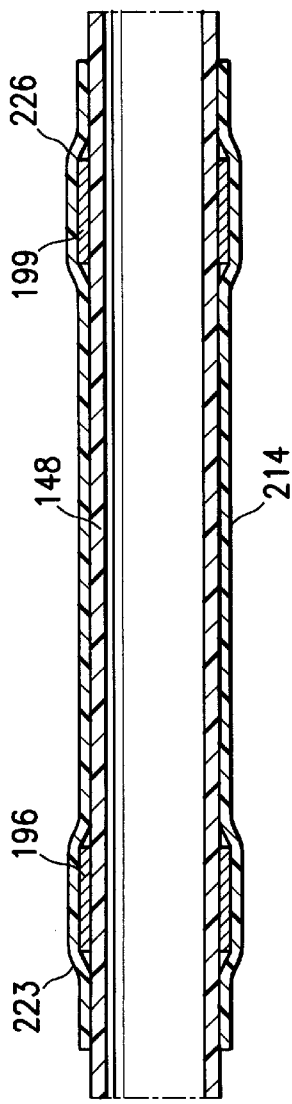

CATHETERS WITH IMPROVED TRANSITION

RELATED APPLICATIONS

This application claims the benefit of U.S. Provisional Application No. 60/164,600, filed Nov. 10, 1999, and assigned to the assignee of the present invention.

FIELD OF INVENTION

The invention relates to the field of intravascular delivery systems, and more particularly to balloon catheters for stent delivery in the intracranial vasculature, referred to herein as neurovasculature.

BACKGROUND OF THE INVENTION

In neurovascular angioplasty procedures a guiding catheter is advanced until the distal tip of the guiding catheter is just proximal to the origin of the intracranial arteries that lead to the target vascular site. A guidewire, positioned within an inner lumen of a dilatation catheter, is first advanced out of the distal end of the guiding catheter into the patient's intracranial vasculature until the distal end of the guidewire crosses a lesion to be dilated. Then the dilatation catheter, having an inflatable balloon on the distal portion thereof, is advanced into the patient's intracranial vasculature over the previously introduced guidewire until the balloon of the dilatation catheter is properly positioned across the lesion. Once properly positioned, the dilatation balloon is inflated with liquid saline or radiopaque contrast one or more times to a predetermined size at relatively high pressures (e.g. at least about 4–6 atmospheres) so that the lesion is dilated to restore vessel patency. However, damage to the vessel wall at and around the lesion can result from the expansion of the balloon against the vessel wall. After the balloon is finally deflated, blood flow resumes through the dilated vessel and the dilatation catheter can be removed therefrom.

In such neurological angioplasty procedures, there may be restenosis of the lesion due to acute or sub-acute (chronic) complications, such as vessel recoil, lesion dissection, intimal hyperplasia, or other factors. The resulting restenosis may in turn necessitate either another angioplasty procedure, or some other method of repairing or strengthening the dilated area. In similar coronary angioplasty, the restenosis rate is reduced and the dilated area is strengthened by implanting an intravascular prosthesis, generally called a stent, inside the artery at the site of the lesion. However, currently, this treatment modality is not available in neurovascular applications due primarily due to the inability to access the distal, highly tortuous anatomy of the neurovascular system with conventional stent delivery systems. Further details of stents and stent delivery systems for PTCA procedures can be found in U.S. Pat. No. 5,507,768 (Lau et al.), U.S. Pat. No. 5,458,615 (Klemm et al.), and U.S. Pat. No. 5,514,154 (Lau et al.), which are incorporated herein by reference in their entireties. Commonly used coronary stent delivery systems are too inflexible to track through the neuro anatomy. Furthermore, they tend to kink when bent into tight radius curves.

Therefore, what has been needed is a catheter and stent delivery system suitable for use in neurovascular applications. The present invention satisfies these and other needs.

SUMMARY OF THE INVENTION

The present invention is directed to a balloon catheter, such as a dilatation catheter and a stent delivery catheter with improved stiffness transition and specifically with no sudden changes in stiffness along the catheter length. In the balloon catheters of the invention alone or mounted with a stent, whether used for peripheral, coronary, or neurovascular applications, is important to reduce the significant bending stiffness changes (herein referred to as bending stiffness discontinuity) present along the length of the catheter. It should also be appreciated that although in describing features of the present invention, the features are directed primarily to a neurovascular stent delivery system, the invention is also applicable to coronary and peripheral stent delivery systems, as well as dilatation catheters for peripheral, neurological, coronary, and similar applications.

Having smooth transitions from one region to another along the length of the catheter, in particular, when a stent is located on the catheter, is of particular importance in neurovascular applications. The major design challenge for a Neurovascular Stent Delivery System (NSDS), in particular, has been in improving the ability to access the distal, highly tortuous anatomy of the neurovascular system. In order to meet this challenge, the present invention provides for a catheter and stent delivery system optimized for flexibility and kink-resistance. Improved flexibility allows the device to turn tight corners along the vasculature without applying large forces against the wall of the vessels, thus minimizing the surface friction between the catheter and the vessel. This allows more distal access, particularly in tortuous neurovascular anatomy.

The optimization of flexibility for the neurovascular stent delivery system may aggravate the kinking dynamic, as for example, bending stiffness discontinuities can be more pronounced as some softer catheter members are more likely to kink than stiffer members. Kinking of the catheter is also a common constraint to distal access. The kink creates a hinge point in the catheter so that the catheter can no longer navigate tight radius turns in the vasculature. Kinks often occur at the interface of two regions along the device having substantially different bending stiffness (i.e., have a discontinuity in the bending stiffness). Examples of such interfaces, include, but are not limited to: the proximal and distal ends of a stent disposed on a catheter, and areas adjacent the balloon seals and marker bands.

The stent delivery system of the present invention, in particular as adapted for neurovascular applications, has been optimized for flexibility and kink resistance. The kink resistance has been achieved by minimizing the differential in bending stiffness at the troublesome regions. The present invention includes various embodiments for minimizing the bending stiffness differential as well as increasing the overall flexibility of the catheter, including but not limited to one or more of the following: (1) the lengthening and softening of the catheter tip and the distal balloon seal while maintaining a low profile, (2) crimping the ends of the stent onto the marker bands, (3) locating stiffening sleeves on the inner member on or near the ends of the stent, (4) using a variable stiffness inner member, and (5) providing variable stiffness sheath on the catheter particularly over the stent; in order to reduce the stiffness differential among adjacent portions along the catheter.

In the practice of the present invention, the areas of low bending stiffness located immediately before or after an area of higher bending stiffness may be "built up" in stiffness to gradually transition the stiffness of that portion to an adjacent portion of higher value, thus providing a relatively smooth transition from one region to another.

In other words, the present catheter has more than one portion with different stiffness values, each portion comprising of components that gradually transition the stiffness of that portion to an adjacent portion, thus reducing the differential in bending stiffness in moving from one region to another, when the catheter is used alone or in combination with a stent in a stent delivery system.

The stent delivery system of the present invention includes a catheter having an elongated shaft with proximal and distal ends and an inner lumen extending therein. The system further includes an enlargable member mounted on a distal shaft section proximal to the distal end which is configured for supporting a deployable prosthetic device on a receiving portion thereon. The enlargable member has an interior in fluid communication with the inner lumen. Furthermore, a tubular member extends through the interior of the enlargable member.

In one embodiment, the stent delivery system further includes proximal and distal radiopaque markers disposed on a portion of the tubular member extending within the interior of the enlargable member. Preferably, a portion of each marker is within and a portion is outside the receiving portion of the enlargable member. Optionally, the catheter system may further include at least one jacket disposed on a portion of the tubular member extending within the interior of the enlargable member. The jacket overlays, at least in part, at least one of the proximal and distal markers. The jacket, preferably, extends, at least in part, outside the receiving portion of the enlargable member. The jacket may include an outer and an inner layer. A portion of the inner layer is adjacent the tubular member extending through the interior of the enlargable member. The system may further include at least one outer jacket formed of a material relatively stiffer than the jacket material. The outer jacket butts up to at least one of the proximal and distal markers. The at least one outer jacket may be, at least partially, overlaid with the jacket.

Alternatively the stent delivery system further includes more than one portion with different stiffness values. Each portion comprises of components that gradually transition the stiffness of that portion to an adjacent portion. Preferably, the stiffness ratio between any two adjacent portions is at least 0.3, more preferably from about 0.3 to about 0.7, and most preferably, at least 0.7. Alternatively, the system further include an outer tubular member and an inner tubular member. The outer tubular member may include more than one section, the sections having a decrease in stiffness in the distal direction. The inner member may include more than one section, the sections having a decrease in stiffness in the distal direction. Alternatively, the stiffness of a portion of the inner tubular member may be built up to more smoothly match the stiffness of an adjacent portion of higher stiffness. Alternatively, the system may further include proximal and distal radiopaque markers disposed on a portion of the tubular member extending within the interior of the enlargable member. Alternatively, the at least one portion of the tubular member extending within the interior of the enlargable member includes a tubular member with an imbedded coil for providing a gradual transition in stiffness of that portion to the enlargable member receiving portion upon receiving the deployable member thereon. Alternatively, the system may further include a retractable sheath disposed over at least a portion of the catheter shaft for covering the deployable member once the deployable member is mounted on the catheter. The sheath, preferably, has a variable stiffness to minimize kinking of the catheter near or at proximal and distal ends of the deployable member.

In another embodiment, the stent delivery system further includes at least one radiopaque segment having proximal and distal ends. The at least one radiopaque segment is disposed, at least in part, within the enlargable member. The catheter shaft has a sufficiently gradual change in stiffness from a point proximal to the proximal end of the radiopaque segment to at least the proximal end of the radiopaque segment to minimize kinking of the catheter upon application of force during a medical procedure. Additionally, the enlargable member includes a deployable member receiving portion having proximal and distal receiving ends with the at least one radiopaque segment located longitudinally within and outside the deployable receiving portion. Alternatively, the radiopaque segment has a conical shape with a conicity away from the receiving portion. Alternatively, the radiopaque segment is integral with the tubular member extending through the enlargable member.

Alternatively, the stent delivery system further includes an outer tubular member and an inner tubular member with a distal inner member having a portion extending through the enlargable member. The extending portion of the distal inner member includes at least one tubular sleeve disposed about and attached to the distal inner member. The at least one tubular sleeve has sufficient stiffness to provide a relatively smooth stiffness transition from a point along the catheter shaft proximal to a proximal edge of the at least one tubular sleeve to a point along the catheter shaft distal to a distal edge of the at least one tubular sleeve. Additionally, the proximal tubular sleeve is extended into a distal end of the outer tubular member forming a proximal overlap region to minimize proximal transition kinking. Optionally, a portion of the distal end of the outer tubular member is extended into the proximal section of the enlargable member and the proximal overlap is located within the extended portion.

In another embodiment, the stent delivery system further includes an outer tubular member having a distal edge and an inner tubular member. The distal edge of the outer tubular member extends distally to a point being at the same transverse location or proximal to a proximal end of the receiving portion. Optionally, the distal edge of the outer tubular member may extend distal to the proximal end of the receiving portion.

In another embodiment, the stent delivery system the enlargable member forms proximal and distal fluid-tight seals with the catheter shaft at the enlargable member proximal end and distal ends, respectively. The distal seal of the enlargable member may have perforations or grooves thereon to provide a gradual stiffness reduction in the distal direction.

In another embodiment, the stent delivery system further includes a catheter tip at the shaft distal end and includes an atraumatic distal tip having a distal end. The tubular member extending through the enlargable member has a distal end which is butt-joined to a proximal end of the atraumatic distal tip. An outer layer member may be butt-jointed or lap-jointed to the distal end of the enlargable member at a point proximal to the tubular member distal end. The outer layer extends distally to a point proximal to the distal end of the atraumatic distal tip.

The balloon catheter of the present invention includes a catheter having an elongated shaft with proximal and distal ends and an inner lumen extending therein. The system further includes an enlargable member mounted on a distal shaft section proximal to the distal end. The enlargable member has an interior in fluid communication with the inner lumen. Furthermore, a tubular member extends through the interior of the enlargable member.

In one embodiment, the balloon catheter further includes proximal and distal radiopaque markers disposed on a portion of the tubular member extending within the interior of the enlargable member. Optionally, the balloon catheter may further include at least one jacket disposed on a portion of the tubular member extending within the interior of the enlargable member. The at least one jacket overlays, at least in part, at least one of the proximal and distal markers.

Alternatively the balloon catheter further includes more than one portion with different stiffness values. Each portion comprises of components that gradually transition the stiffness of that portion to an adjacent portion. Preferably, the stiffness ratio between any two adjacent portions is at least 0.3, more preferably from about 0.3 to about 0.7, and most preferably, at least 0.7. Alternatively, the balloon catheter further include an outer tubular member and an inner tubular member. The outer tubular member may include more than one section, the sections having a decrease in stiffness in the distal direction. The inner member may include more than one section, the sections having a decrease in stiffness in the distal direction. Alternatively, the stiffness of portion of the inner tubular member may be built up to more smoothly match the stiffness of an adjacent portion being of higher stiffness. Alternatively, the balloon catheter may further include proximal and distal radiopaque markers disposed on a portion of the tubular member extending within the interior of the enlargable member. Alternatively, the at least one portion of the tubular member extending within the interior of the enlargable member includes a tubular member with an imbedded coil for providing a gradual transition in stiffness of that portion to an adjacent portion of higher stiffness. Alternatively, the balloon catheter may further include a sheath disposed over at least a portion of the enlargable member. The sheath, preferably, has a variable stiffness to minimize kinking of the catheter near or at the enlargable member.

In another embodiment, the balloon catheter further includes at least one radiopaque segment having proximal and distal ends. The at least one radiopaque segment is disposed, at least in part, within the enlargable member. The catheter shaft has a sufficiently gradual change in stiffness from a point proximal to the proximal end of the radiopaque segment to at least the proximal end of the radiopaque segment to minimize kinking of the catheter upon application of force during a medical procedure. Additionally, at least one radiopaque segment may be located longitudinally within the interior of the enlargable member. Alternatively, the radiopaque segment has a conical shape with a conicity away from the intermediate section of the enlargable member. Alternatively, the radiopaque segment is integral with the tubular member extending through the enlargable member.

Alternatively, the balloon catheter further includes an outer tubular member and an inner tubular member with a distal inner member having a portion extending through the enlargable member. The extending portion of the distal inner member includes at least one tubular sleeve disposed about and attached to the distal inner member. The at least one tubular sleeve has sufficient stiffness to provide a relatively smooth stiffness transition from a point along the catheter shaft proximal to a proximal edge of the at least one tubular sleeve to a point along the catheter shaft distal to a distal edge of the at least one tubular sleeve. Additionally, the proximal tubular sleeve is extended into a distal end of the outer tubular member forming a proximal overlap region to minimize proximal transition kinking. Optionally, a portion of the distal end of the outer tubular member is extended into the proximal section of the enlargable member and the proximal overlap is located within the extended portion.

In another embodiment, the balloon includes proximal and distal sections with an intermediate section therebetween. The balloon catheter further includes an outer tubular member having a distal edge and an inner tubular member. The distal edge of the outer tubular member extends distally within the intermediate portion of the enlargable member. Optionally, the distal edge of the outer tubular member may extend distal to a proximal end of the intermediate section.

In another embodiment, the enlargable member of the balloon catheter forms proximal and distal fluid-tight seals with the catheter shaft at the enlargable member proximal end and distal ends, respectively. The distal seal of the enlargable member may have perforations or grooves thereon to provide a gradual stiffness reduction in the distal direction.

In another embodiment, the balloon catheter further includes a catheter tip at the shaft distal end and includes an atraumatic distal tip having a distal end. The tubular member extending through the enlargable member has a distal end which is butt-joined to a proximal end of the atraumatic distal tip. An outer layer member may be butt-joined to the distal end of the enlargable member at a point proximal to the tubular member distal end. The outer layer extends distally to a point proximal to the distal end of the atraumatic distal tip.

BRIEF DESCRIPTION OF THE DRAWINGS

FIG. 1 is a longitudinal cross sectional view of a stent delivery system embodying features of the invention.

FIG. 2 is a transverse cross sectional view of the delivery system of FIG. 1 taken along line 2—2.

FIG. 3 is a transverse cross sectional view of the delivery system of FIG. 1 taken along line 3—3.

FIG. 6(A) is a longitudinal cross sectional view, in part, of an alternative embodiment of a delivery system having an outer and inner tubular member with the inner tubular member having at least one tubular sleeve disposed about and attached to a portion thereof.

FIG. 6(B) is an alternative embodiment of the system of FIG. 6(A) having at least one radiopaque marker disposed on the inner tubular member and in contact with the at least one tubular sleeve.

FIGS. 10(A) through 10(E) are longitudinal cross sectional views, in part, of alternative embodiments of FIG. 9 showing the markers and the one or more jackets.

DETAILED DESCRIPTION OF THE INVENTION

Figure 4:
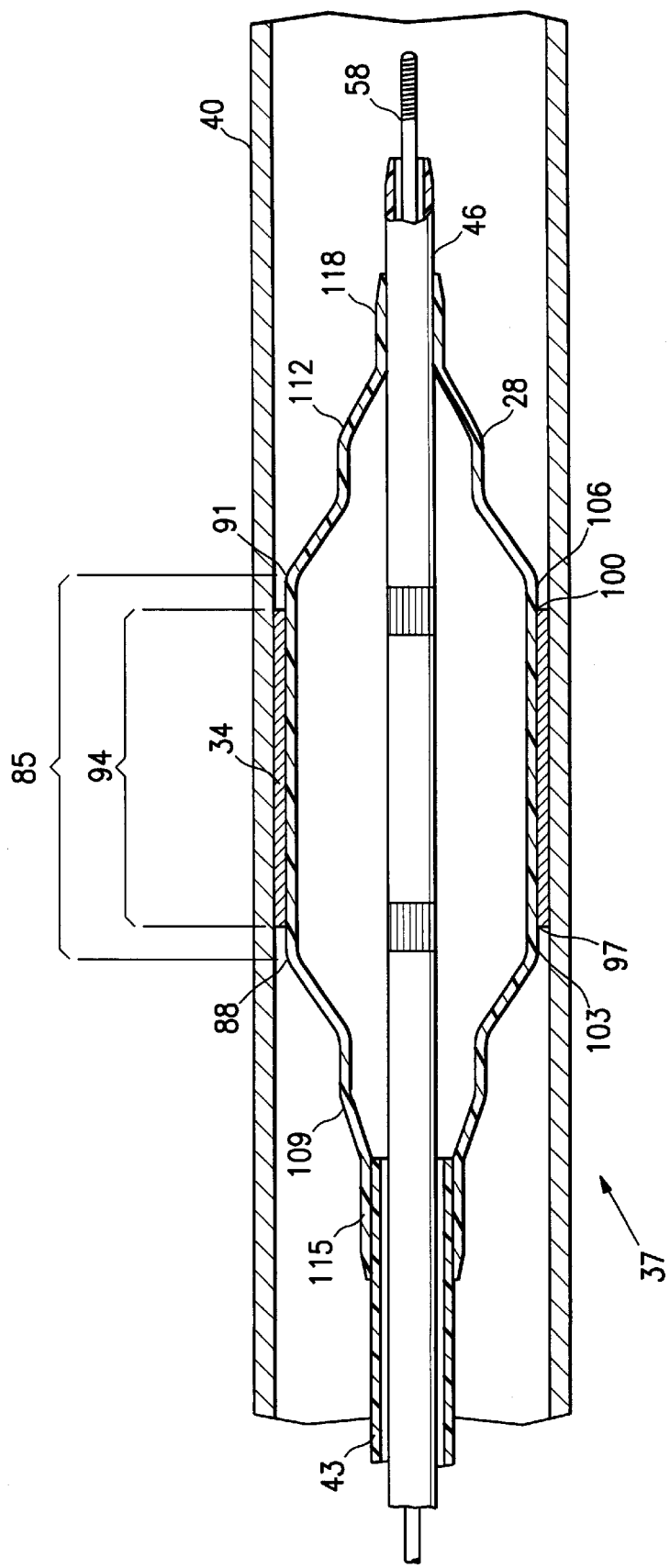
FIG. 4 is a longitudinal cross sectional view of the system of FIG. 1 showing an inflatable member in the inflated condition.

FIG. 1 illustrates a balloon catheter 10 embodying features of the invention. The balloon catheter 10 of the invention generally includes an elongated catheter shaft 13 having a proximal section 16 and a distal section 19 with a distal end 22 and a distal tip 25, an enlargable member such as an inflatable balloon 28 on the distal section 19 of the catheter shaft 13, and an adapter 31 mounted on the proximal section 16 of the catheter shaft 13. In the embodiment illustrated in FIG. 1, the balloon catheter 10 has a stent 34 mounted on the balloon 28 to form a stent delivery catheter system 37. In FIG. 1, the catheter system 37 is illustrated within a patient's body lumen 40 prior to expansion of the balloon 28, with the balloon 28 and stent 34 in a low profile, unexpanded state for advancement within the patient.

In the embodiment illustrated in FIG. 1, the catheter shaft 13 has an outer tubular member 43 and an inner tubular member 46 disposed within the outer tubular member 43 and defining, with the outer tubular member, an inflation lumen 49. The inflation lumen 49 is in fluid communication with an interior chamber 52 of the inflatable balloon 28. The inner tubular member 46 has an inner lumen 55 extending therein configured to slidably receive a guidewire 58 suitable for advancement through a patient's vasculature. A distal extremity 61 of the inflatable balloon 28 is sealingly secured to a distal extremity 64 of the inner tubular member 46 to form a distal seal 67 at distal junction 70 and a proximal extremity 73 of the balloon 28 is sealingly secured to a distal extremity 76 of the outer tubular member 43 to form a proximal seal 79 at a proximal junction 82. FIGS. 2 and 3 illustrate transverse cross sectional view of the catheter 10 shown in FIG. 1, taken along lines 2—2 and 3—3, respectively.

As best illustrated in FIG. 4, the balloon 28 has an intermediate section 85 located thereon, preferably centrally, with proximal and distal intermediate ends, 88 and 91. The intermediate section 85 includes a stent-receiving portion 94 with proximal and distal receiving ends, 97 and 100, respectively, for receiving a stent thereon, and proximal and distal intermediate portions 103 and 106, adjacent the proximal and distal receiving ends, 97 and 100, respectively. However, it is possible for all or part of the stent-receiving portion 94 to coincide with the intermediate section 85. The balloon 28 further includes a proximal tapered area 109 adjacent the proximal end 88 of the intermediate section 85 and a distal tapered area 112 adjacent the distal end 91 of the intermediate section 85. The proximal and distal tapered areas 109 and 112 taper down to a proximal and distal shaft 115 and 118, respectively. The proximal balloon shaft 115 and the distal balloon shaft 118 are secured to the outer tubular member 43 and the inner tubular member 46, respectively, using a variety of suitable means such as adhesive and fusion bonding.

In operation, when the stent 34 is mounted on the stent-receiving portion 94 of the balloon 28, the proximal and distal intermediate portions, 103 and 106, are first expanded at a first pressure, with the stent-receiving portion 94 still in a substantially in an uninflated low profile configuration. The proximal and distal intermediate portions, 103 and 106, expand together at the first pressure to an inflated outer diameter which is greater than the uninflated outer diameter of stent-receiving portion 94 and the stent 34 thereon. As best illustrated in FIG. 4, when the inflation pressure is increased to the deployment pressure of the stent 34, the stent-receiving portion 94 expands against the vessel wall to expand the stent 34 thereon or to dilate a stenosis.

Referring back to FIG. 1, the catheter shaft 13 will generally have the following dimensions. The length of the catheter shaft 13 may be from about 75 cm to about 175 cm, and in the neurovascular application it is typically about 160 cm. The outer tubular member 43 has a length of approximating that of the shaft 13 with an outer diameter (OD) of about 0.030 inches (in) to about 0.060 in, and an inner diameter (ID) of about 0.025 to about 0.050 in. The inner tubular member 46 has a length of about 160 cm, an OD of about 0.018 to about 0.035 in and an ID of about 0.014 to about 0.020 in. The outer and inner tubular members, 43 and 46, may taper in the distal direction to a smaller OD or ID.

The catheter includes more than one portion with different stiffness values, one or more portions comprising of components that gradually transition the stiffness of that portion to an adjacent portion. Preferably, the stiffness of a relatively distal portion is less than the stiffness of a portion immediately proximal to that relatively distal portion. It should however be appreciated that in some portions of the catheter the stiffness of a first portion may be built up, with additional elements or by modifying existing elements, to about the stiffness of a second higher stiffness portion adjacent the first portion in order effectuate a smoother stiffness transition from the first portion to the adjacent second portion of initially higher stiffness. This, for example, may occur with respect to the stent receiving portion and adjacent areas on either or both its proximal and distal sides wherein the stiffness of the inner member proximal to the proximal receiving end is built up to about the stiffness of the receiving portion with a stent mounted thereon, with building down of the stiffness in moving from the distal receiving end toward the distal end of the catheter. In particular, when the catheter is used as a stent delivery catheter, the various portions of the catheter shaft are designed to allow for a smooth transition in stiffness between adjacent portions when a stent is mounted on the catheter.

In a preferred embodiment the stiffness ratio between any two adjacent portions is at least about 0.3, more preferably, between about 0.3 to about 0.7, and most preferably, greater than about 0.7. Additionally, the illustrated marker positions, as for example illustrated in FIG. 1, are representative of one embodiment and although markers 193 may be shown in any of the Figures, such as FIG. 1, the location of the markers are not limited to that illustrated.

In order to achieve the stent delivery catheter system 37 of the present invention having improved stiffness transition profile, the catheter 10 may further include one or more of the features further described below.

Figure 5A:
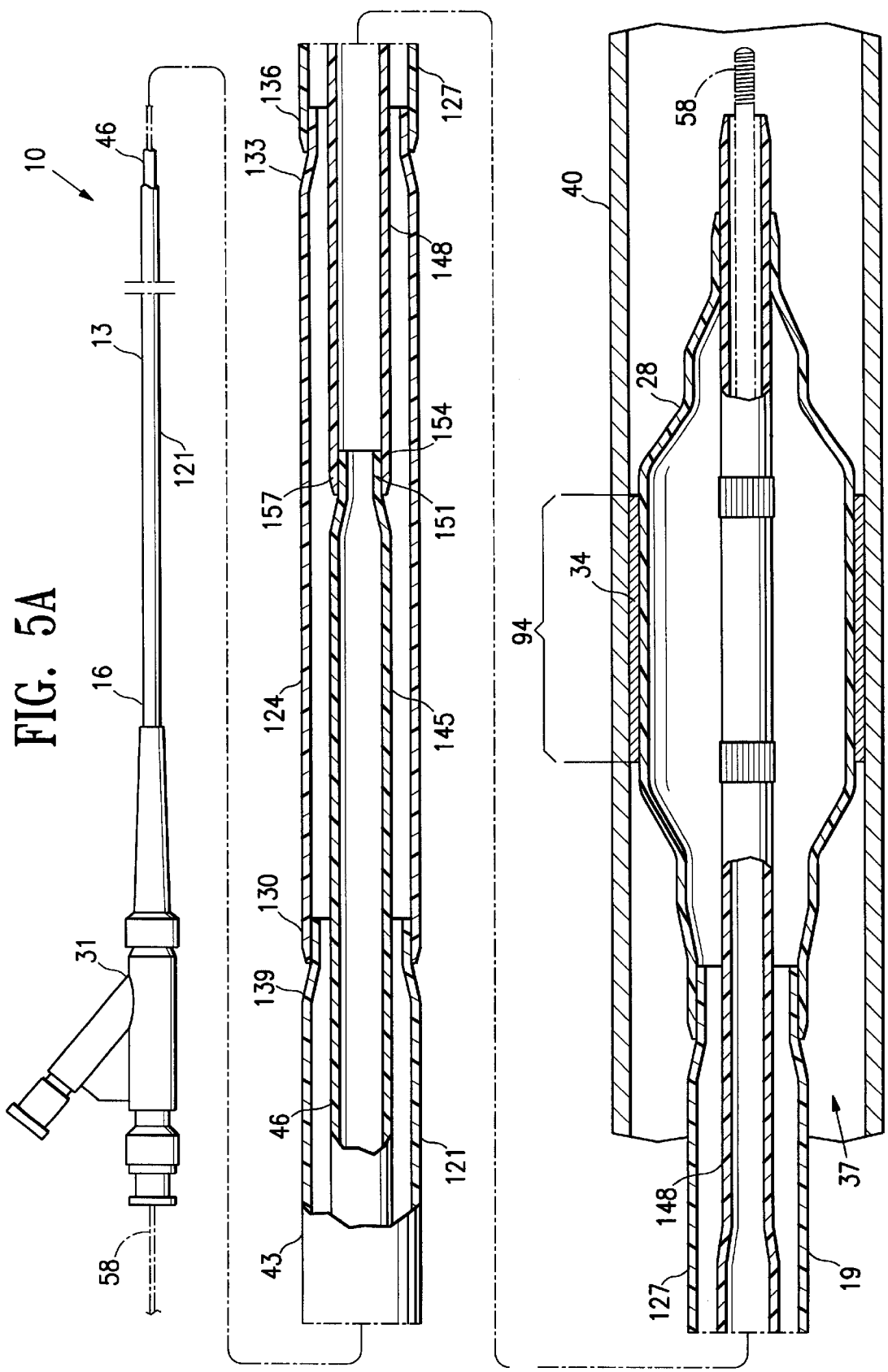
FIG. 5(A) is a longitudinal cross sectional view of an alternative embodiment of a delivery system having an outer and inner tubular member with multiple sections.

In one embodiment, features of which are illustrated in FIG. 5(A), the outer tubular member 43 includes multiple sections, such as the proximal outer member 121, the intermediate outer member 124, and the distal outer member 127, the sections decreasing in stiffness in the distal direction. In the embodiment featured in FIG. 5(A), the intermediate outer member 124 has a proximal end 130 and a distal end 133, with the distal end 133 being necked down, enabling the intermediate outer member 124 to join, at its distal end 133 with a proximal end 136 of the distal outer member 127. Similarly, the proximal outer member 121 at a distal end 139 is necked down, enabling the proximal outer member 121 to join, at its distal end 139 with the proximal end 130 of the intermediate outer member 124.

The multiple stage (sectioned) outer tubular member. 43 with decreasing relative bending stiffness in the distal direction improves the compressive loading efficiency of the catheter 10 while maximizing the flexibility of the catheter 10 at its distal section 19. The relative stiffness of the proximal outer member 121 improves push transmission. The intermediate outer member 124 is of such longitudinal dimension that the distal end 133 of the intermediate outer member 124 does not enter the region of greatest tortuosity within the intracranial vasculature. The moderate flexibility of the intermediate outer member 124 maintains push efficiency while lessening the likelihood of vessel trauma. The distal outer member 127 is relatively flexible and is of sufficient longitudinal dimension to negotiate the stent 34 through highly tortuous anatomy. Additionally, the gradual change in the stiffness minimizes the likelihood of kinking.

In a preferred embodiment, the proximal, intermediate, and distal outer member sections 121, 124, and 127, will be formed of material having flexural modulus stiffness values in a range from about 50 to about $200 \times 10^4$ lb/in$^2$, from about 5 to about $6 \times 10^4$ lb/in$^2$, and from about 1.3 to about $1.7 \times 10^4$ lb/in$^2$, respectively. Preferred material for forming sections 121, 122, and 127 include, respectively, polyetheretherketone (PEEK), polyetherimide (PEI) such as those sold commercially under the ULTEM designation by General. Electric, and stainless steel; polyether block amide (PEBA) such as those sold commercially under the PEBAX® trademark by companies such as Elf Atochem, in particular PEBAX® 63D or 70D; and PEBAX® 40D (Shore D scale). In a preferred embodiment, the proximal, intermediate, and distal outer member sections 121, 124, and 127 will have a longitudinal dimension ranging from about 100 to about 125 cm, from about 25 to about 50 cm, and from about 10 to about 35 cm, respectively, and preferably, being about, 125, 25, and 10 cm, respectively. The outer tubular member 43, preferably, will have an outer diameter ranging from about 0.044 to about 0.054 in, and more preferably, being about 0.050 in, although the outer diameter of the outer tubular member 43 may also taper in the distal direction. The outer tubular member 43, preferably, will have an inner diameter ranging from about 0.034 to about 0.044 in, more preferably, being about 0.040 in.

The inner tubular member 46 includes multiple sections, such as, the proximal inner member 145 and the distal inner member 148, the sections decreasing in stiffness in the distal direction. In the embodiment featured in FIG. 5(A), the proximal inner member 145 is necked down at a distal end 151 to form an inner member junction 154 with a proximal end 157 of the distal inner member 148. Preferably, the junction 154 is located along the longitudinal axis of the catheter 13 within either the proximal or the intermediate outer-tubular members, 121 and 124. More preferably, the junction 154 does not coincide with the junctures between the intermediate outer member 124 and the proximal and distal outer members 121 and 127.

The multiple stage (sectioned) inner tubular member 46 with a relatively stiff proximal inner member 145 and a relatively flexible distal inner member 148 improves the compressive loading efficiency of the catheter 10 while minimizing the floppiness of the overall inner member 46 resulting in less deflection of the catheter tip 25 (FIG. 1) when being advanced through the anatomy. Additionally, by placing the junction 154 within a relatively stiff outer tubular member 43, in other words the proximal 121 or the intermediate 124 outer tubular members, the bending stiffness dislocation at the inner member junction 154 is minimized.

In a preferred embodiment, the proximal and distal inner member sections 145 and 148, will be formed of material having flexural modulus in a range from about 50 to about $200 \times 10^4$ lb/in$^2$, and from about 1.3 to about 5 lb/in$^2 \times 10^4$. Preferred material for forming sections 145 and 148 include, respectively, PEEK, and a co-extrusion comprising PEBA (e.g. PEBAX 40D) and high density polyethylene (HDPE) with a layer of an ethylene and acrylic acid copolymer such as PRIMACOR 1420 therebetween. In a preferred embodiment, the proximal and distal inner member sections 145 and 148 will have a longitudinal dimension ranging from about 125 to about 140 cm and from about 20 to about 35 cm, respectively, preferably, being about 135 and 25 cm, respectively. The inner tubular member 46, preferably, will have an outer diameter ranging from about 0.020 to about 0.035in, although outer diameter of the inner tubular member 46 may also taper in the distal direction. The inner tubular member 46, preferably, will have an inner diameter ranging from about 0.016 to about 0.020, and more preferably, from about 0.016 to about 0.018 in. Additionally, the distal inner member 148 may be necked down, preferably, to an OD of about 0.020 and an ID of about 0.016 at a location proximal to the proximal end of the inflatable member at about 5 cm from the distal tip of the catheter.

Figure 5B:
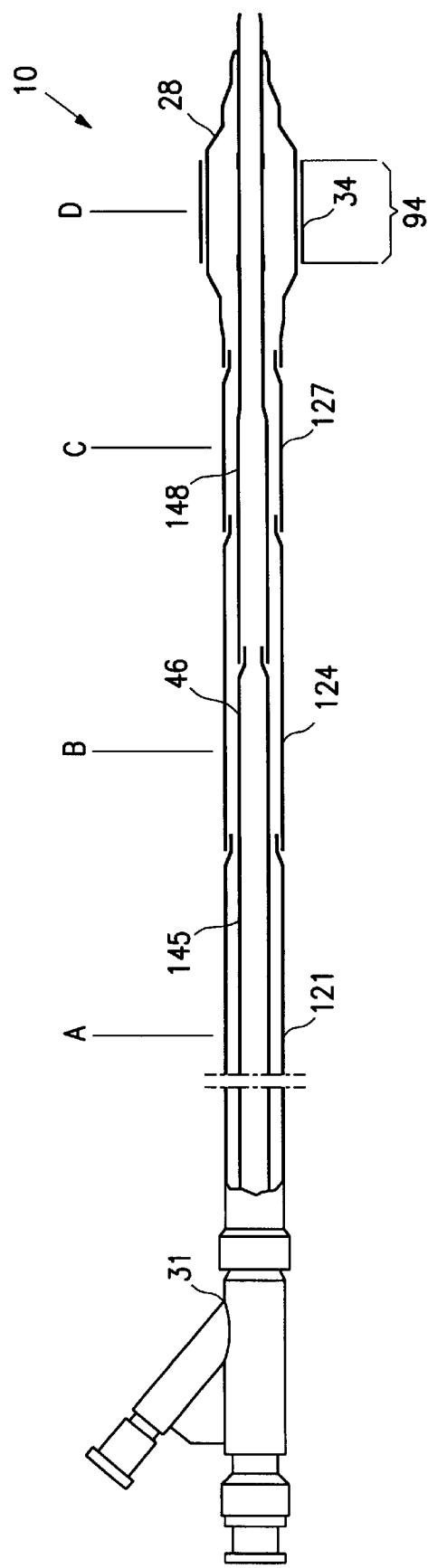
FIG. 5(B) is longitudinal view of an alternative embodiment of the delivery system of FIG. 5(A) having different stiffness ratios along the length of the catheter.

In a preferred embodiment, features of which are illustrated in FIG. 5(B), the stiffness ratio between any two adjacent portions is no less than about 0.3, more preferably, between about 0.3to about 0.7, and most preferably, at least about 0.7 or greater. For example, the stiffness ratio between point "A" and point "B" is about 1 to about 0.64; between points "B" and "C" is about 1 to about 0.3; and between points "C" and "D" is about 0.76 to about 1; with points "A", "B", "C", and "D" being along the following portions of the catheter, respectively; the proximal outer tubular section 121 and the proximal inner tubular member 145; intermediate outer tubular section 124 and the proximal inner tubular section 145; distal outer tubular section 127 and distal inner tubular section 148; and the stent receiving portion 94 with a stent mounted thereon (including other members that may be present in this portion such as inner member, marker, etc.).

In one embodiment, features of which are illustrated in FIG. 6(A), the catheter shaft 13 at one or more portions of the distal inner member 148 extending through the inflatable member 28 includes at least one tubular sleeve 160 disposed about and attached to the distal inner member 148, preferably, a proximal sleeve 163 and a distal sleeve 166. When a stent 34 is present on the catheter, the one or more tubular sleeve 160 has sufficient stiffness to provide a relatively smooth stiffness transition from a point along the catheter shaft 13 proximal to a proximal edge 169 of the stent 34 to the proximal edge 169 of the stent 34, and from the distal edge 172 of the stent 34 to a point along the catheter shaft 13 distal to the distal edge 172 of the stent 34. Additionally, one or more of the tubular sleeves 163 and 166 may also protect the proximal and distal edges 169 and 172 of the stent 34 by providing extra support in the stiffness transition areas. The proximal and distal tubular sleeves 163 and 166 will be of sufficient outer diameter to aid in holding the stent 34 in the desired location and minimize risk of loss during insertion into the vasculature.

Preferably, as illustrated in FIG. 6(A), the proximal sleeve 163 extends proximally to the distal edge 175 of the distal outer member 127 and the distal sleeve 166 extends distally to a proximal edge 178 of the distal balloon shaft 118. The tubular sleeves 163 and 166 may be attached to the distal inner member 148 using a heat-based process and they may be tapered on their respective ends, with the amount of taper designed to provide optimum performance.

The tubular sleeve member 160 is formed of material having a flexural modulus ranging from about 1.3 to about $1.7 \times 10^4$ lb/in$^2$. Suitable materials for forming the tubular sleeve 160 include the same material as those used to form the distal inner member 148, but of softer variety. Exemplary material for use as tubular sleeve 1 60 include, but are not limited to, PEBAX 40D, 63D, or 70D. The tubular sleeve 160, preferably, has a wall thickness ranging from about 0.002 to about 0.005 in.

In another embodiment, features of which are illustrated in FIG. 6(B), the proximal and distal tubular sleeves, 163 and 166, may be used in conjunction with proximal and distal markers. When used in cooperation with markers, as illustrated in FIG. 6(B), the tubular sleeves 163 and 166, will preferably extend distal to the proximal edge 169 of the stent 34 (or proximal receiving end 97) and will extend proximal to the distal edge 172 of the stent (or distal receiving end 100) to minimize kinking.

Figure 7:
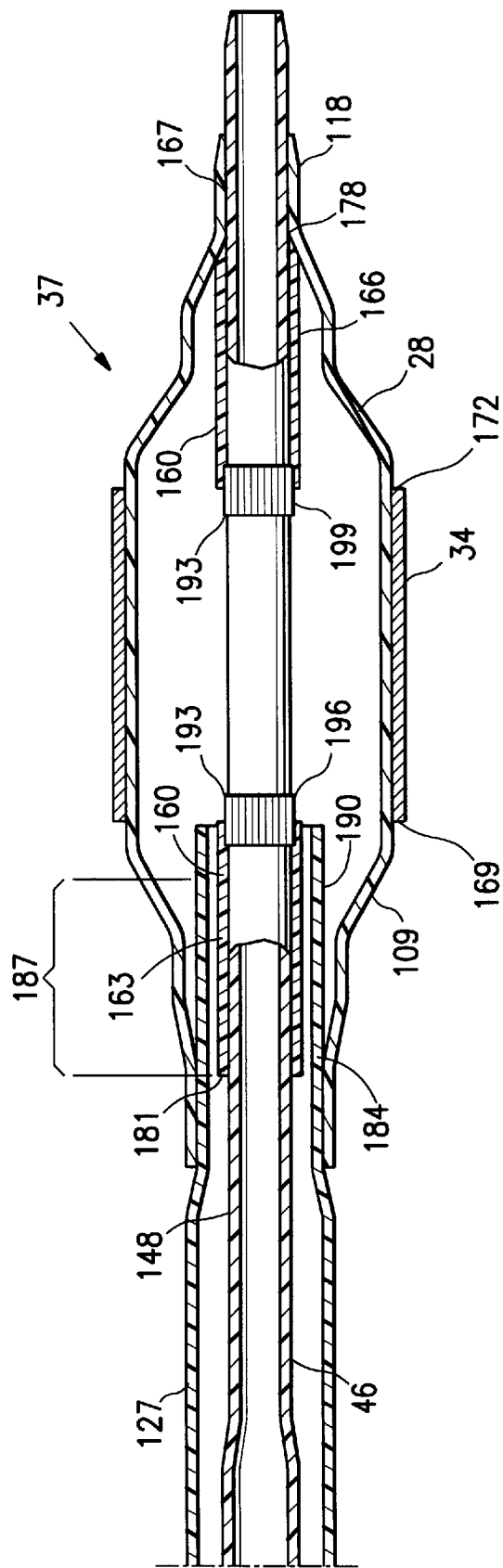
FIG. 7 is an alternative embodiment of the system in FIG. 6(B) showing a proximal end of a proximal tubular sleeve extended into a distal end of the outer tubular member and forming a proximal overlap.

In a preferred embodiment a proximal end 181 of the proximal tubular sleeve 163 is extended into a distal end 184 of the distal outer tubular member 127 forming a proximal overlap region 187 to minimize proximal transition kinking. On the other hand, to minimize the impact of the proximal overlap 187 on inflation/deflation of the inflatable member 28, the overlap 187 is located within the proximal taper section 109 of the inflatable member 28 by extending a portion 190 of the distal end 184 of the distal outer tubular member 127 into the proximal taper section 109. Preferably, as illustrated in FIG. 7, the distal end 184 of the distal outer tubular member 127, and thus the proximal overlap 1 87, extends proximally at least to the proximal edge of the proximal tubular sleeve 163, and more preferably, overlaps at least partially with the proximal tubular sleeve 163. The extended portion 190 of the distal outer member 127 can include slices, holes, perforations or grooves.

Figure 8A:
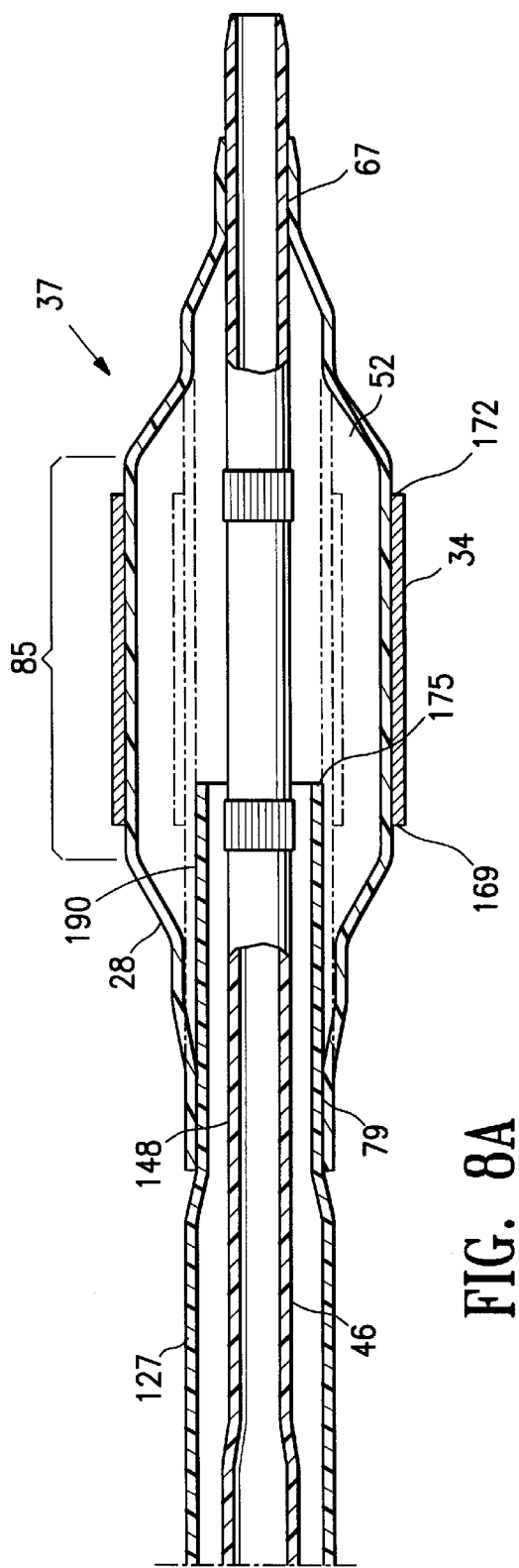
FIG. 8 is a longitudinal cross sectional view, in part, of an alternative embodiment of a delivery system having an outer and an inner tubular member with a distal end of the outer tubular member extended into an inflatable member intermediate area.
Figure 8B:
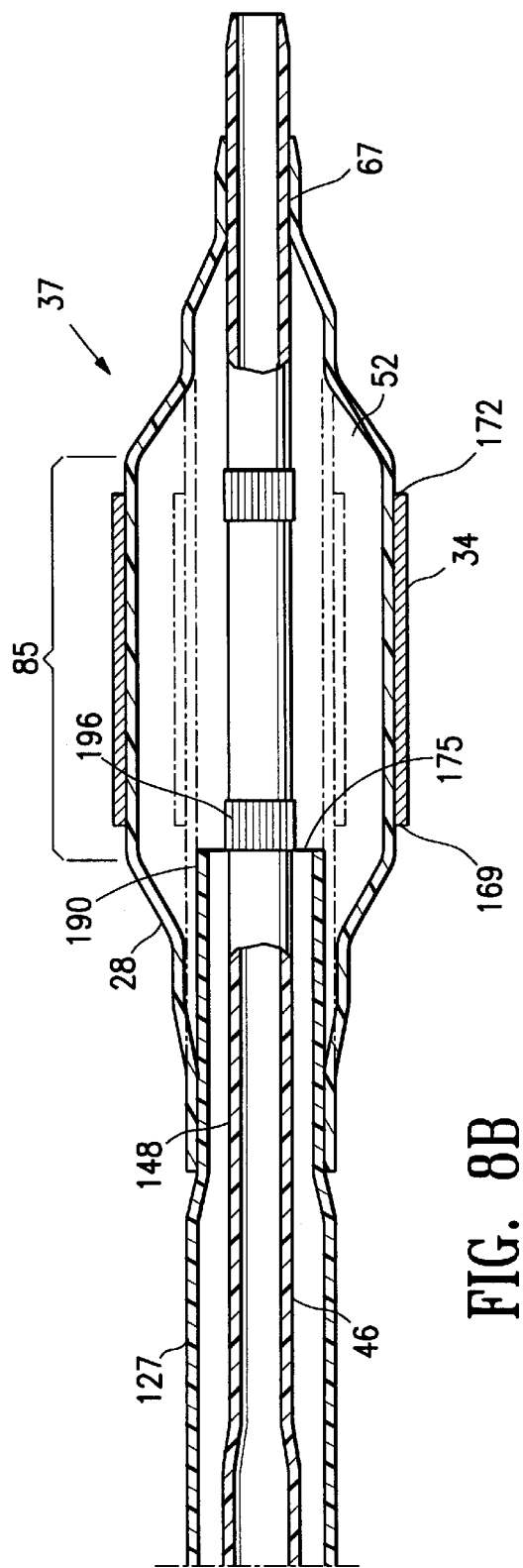

In another embodiment, an extended distal portion 190 of the distal outer member 127 is extended into the balloon interior chamber 52 such that the distal edge 175 of the distal outer member 127 extends at least to the same longitudinal location as the distal end of the proximal seal 79. Preferably, as illustrated in FIG. 8A, the distal outer member 127 is extended into the balloon intermediate section 85 such that the distal edge 175 of the distal outer member 127 extends at least to the same longitudinal location as the proximal edge 169 of the stent 34 (or proximal receiving end 97). More preferably, the distal edge 175 of the distal outer member 127 terminates distal to the proximal edge 169 of the stent 34 (or proximal receiving end 97), as illustrated in FIG. 8A. Extending the distal outer tubular member 127 to or distal to the proximal edge 169 of the stent 34 (or proximal receiving end 97) is an effective way of distributing bending moment across the proximal end of the balloon. In FIG. 8A, the uninflated balloon is illustrated in phantom lines. Optionally, as illustrated in FIG. 8B, when the proximal edge 169 of the stent 34 ends on a marker such as proximal marker 196, the distal edge 175 of the distal outer member 127 can extend to the proximal edge of the proximal marker 169.

In one embodiment, as illustrated in FIG. 8C and 8D, at least a portion of the extended distal portion 190 includes perforations 191 or grooves 192 to either or both facilitate passage of inflation fluid to and from the balloon interior chamber 52 as may be necessary and change the stiffness of the catheter. The perforations 191 can have different shapes, such as circular or oblong. In another embodiment, the inner tubular member 46 (FIG. 9) includes at least one radiopaque marker 193 formed of material including at least in part material such as platinum, gold, tungsten, or tantalum, such that during the medical procedure, the location of the stent 34 within the stent delivery system 37 is identifiable through the use of fluoroscopy.

Figure 9:
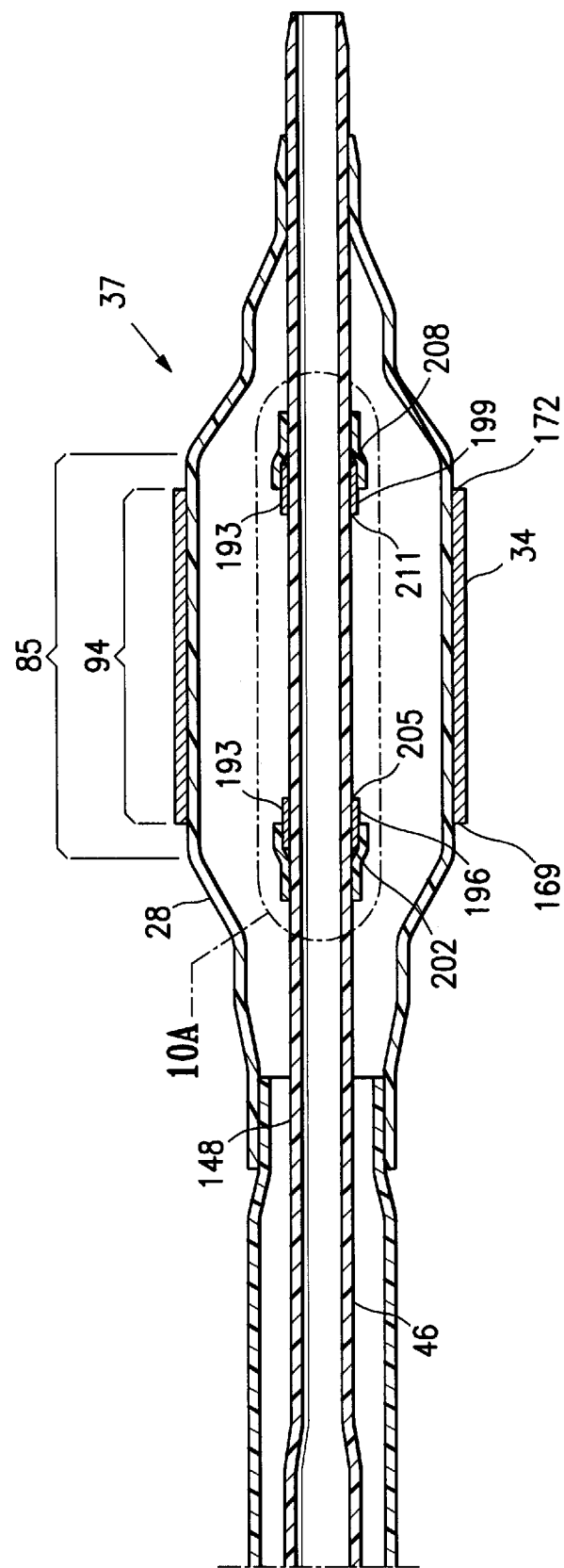
FIG. 9 is a longitudinal cross sectional view, in part, of an alternative embodiment of a delivery system having a proximal and a distal radiopaque marker positioned on an inner member with the proximal marker extending on both sides of a proximal edge of a stent and the distal marker extending on both sides of a distal edge of the stent in addition to having a flexible jacket in contact with each marker.

In an embodiment features of which are illustrated in FIG. 9, there is a proximal marker 196 and a distal marker 199 disposed about the distal inner member 148 within the balloon intermediate section 85.

Preferably, as illustrated in FIG. 9, at least a portion of the proximal and distal markers 196 and 199 is positioned within the receiving portion 94 of the inflatable member 28 with at least a portion being outside the receiving portion 94. For example, a proximal portion 202 of the proximal marker 196 extends proximal to the proximal edge 169 of the stent 34 when the stent 34 is mounted on the catheter (or proximal receiving end 97) with a distal portion 205 of the proximal marker 196 extending distally within the receiving portion 94.

Additionally, a distal portion 208 of the distal marker 199 extends distal to the distal edge 172 of the stent 34 (or distal receiving end 100) with a proximal portion 211 of the distal marker 199 extending proximally within the receiving portion 94.

As illustrated in FIGS. 10(*a*) through 10(*d*), one or all of the markers 193 may be in contact with at least one jacket 214 such as proximal jacket 217 or distal jacket 220, the jackets, preferably, formed of a flexible material. The jackets 217 or 220 may overlay, partially (FIG. 10(a)) or completely (FIG. 10(b)), the proximal and distal, markers, 196 and 199. Alternatively, as illustrated in FIG. 10(c), one jacket 214 may overlay both proximal and distal markers 196 and 199.

Figure 10D:
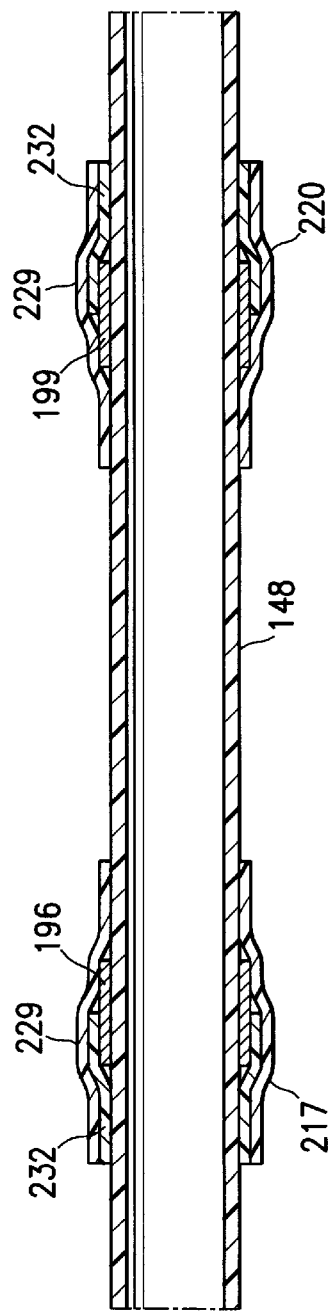

Additionally, as illustrated in FIG. 10(D), either or both the proximal and distal jackets 217 and 220 may comprise of an outer layer 229 and an inner layer 232, a portion of the inner layer 232 being adjacent the distal inner member 148 with the inner layer 232 partially overlaying and the outer layer 229 completely overlaying its respective marker, e.g., proximal marker 196.

Figure 10E:
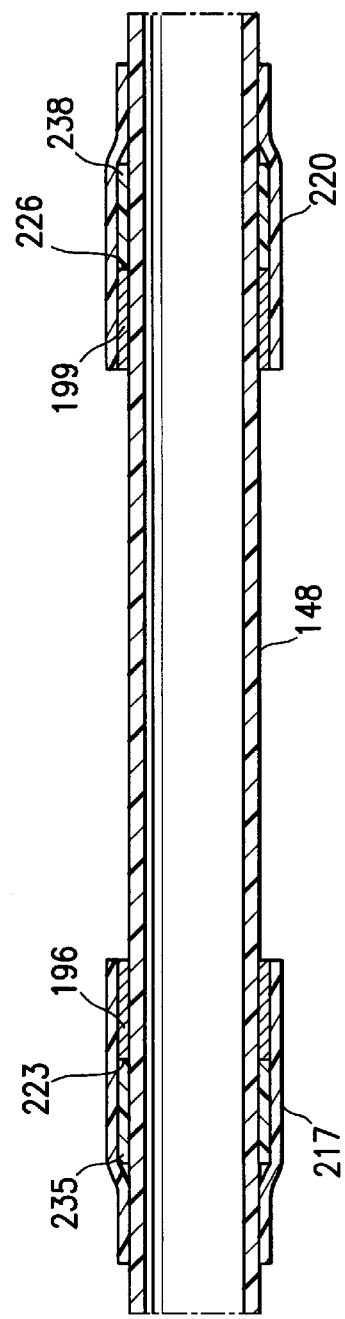

Alternatively, additional proximal outer jacket 235 of relatively stiffer material (FIG. 10(E)) than the proximal jacket 217 may butt up to the proximal marker 196 without overlapping the proximal marker 196. For example, the outer jacket 235 may butt up to the proximal edge 223 of the proximal marker 196 and an additional distal outer jacket 238 may butt up to the distal edge 226 of the distal marker 199. Preferably, as illustrated in FIG. 10(E), the proximal jacket 217 and the distal jacket 220, overlay the proximal outer jacket 235 and the proximal marker 196, and the distal outer jacket 238 and the distal marker 199, respectively.

Figure 11:
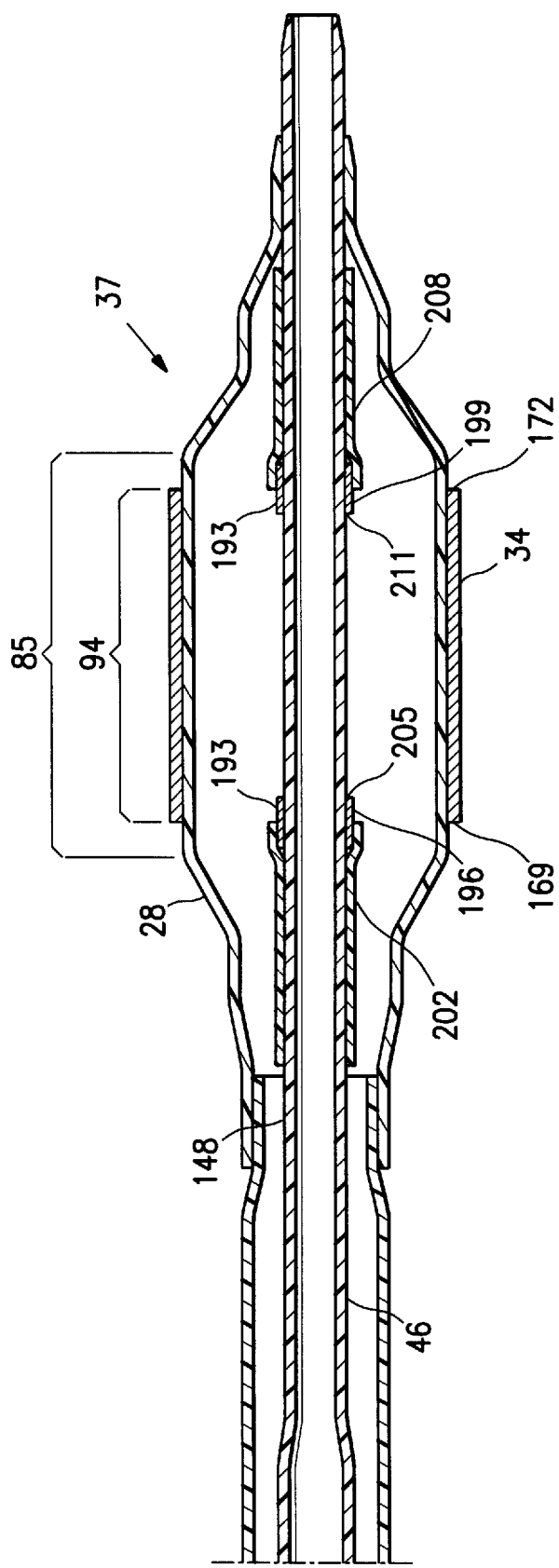
FIG. 11 is a longitudinal cross sectional view, in part, of an alternative embodiment of a delivery system of FIG. 9 with the proximal and distal jackets extending, respectively, proximal and distal to the inflatable member intermediate section.

When present, the proximal jacket 217 extends at least proximal to a proximal edge 223 of the proximal marker 196, preferably extending beyond the proximal edge 223 of the proximal marker 196, and most preferably, extending proximally beyond the inflatable member intermediate section 85; and the distal jacket 220 extends at least distal to a distal edge 226 of the distal marker 199, preferably extending beyond the distal edge 226 of the distal marker 199, and most preferably, extending distally beyond the inflatable member intermediate section 85, as illustrated in FIG. 9, above, and FIG. 11.

The jackets 217 or 220, alone or in combination with the relatively stiffer outer jacket 235 or 238, gradually transition the bending stiffness of the distal inner member 148 to the stiffness of the region of the inner tubular member that includes the markers, in particular when a stent 34 is mounted on the catheter.

Figure 12:
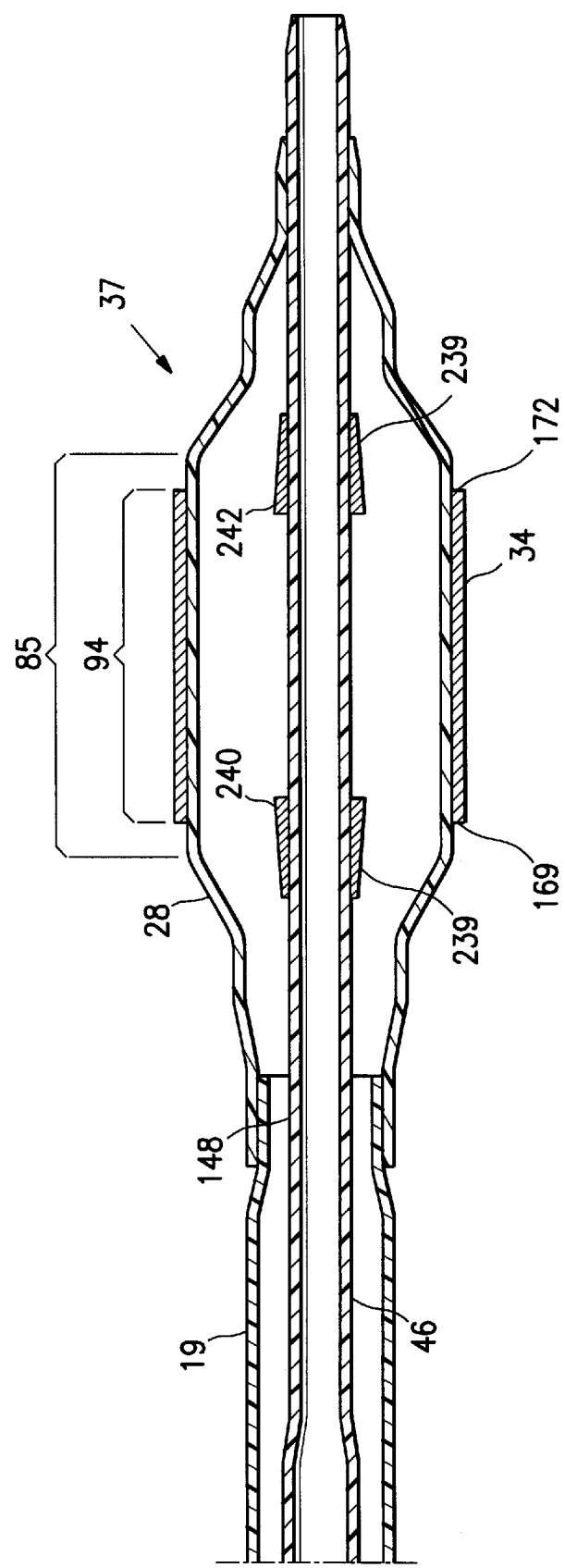
FIG. 12 is a longitudinal cross sectional view, in part, of an alternative embodiment of a delivery system having a conical shaped marker disposed on an inner member.

Now referring to FIG. 12, at least one collar 239, formed of a material comprising, at least in part, a radiopaque material with an increasing outer diameter in the distal direction may be used to provide both the function of the marker 193 and the jacket 214. Preferably, as illustrated in FIG. 12, a proximal 240 and a distal collar 242 is conical in shape with opposite conicities, toward the proximal and distal ends of the catheter, respectively. The proximal and distal collars, 240 and 242, preferably, are of sufficient outer diameter to aid in holding the stent 34 in the desired location and minimize risk of loss during insertion into the vasculature. Exemplary material for forming the collar 239 include, but are not limited to, a radiopaque material such as tantalum or tungsten in a polymeric matrix.

Alternatively, the collar 239 may be integral with the inner tubular member such that the inner tubular member at the desired location has the necessary radiopacity while imparting the desired stiffness profile.

Figure 13A:
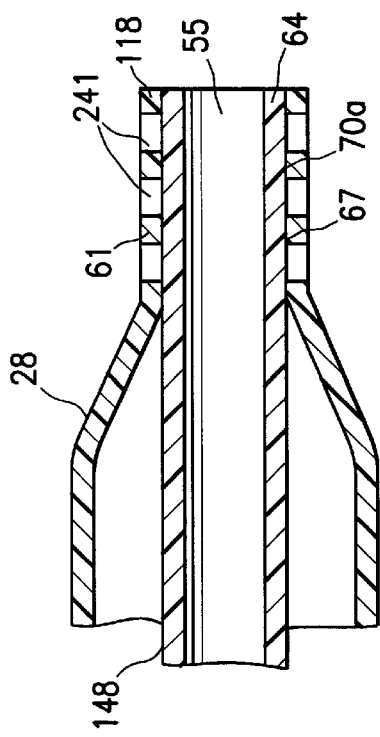
FIGS. 13(A) through 13(C) are cross sectional views, in part, of alternative embodiments of a delivery system having perforations or grooves on a catheter tip.

In an embodiment illustrated in FIG. 13(A), a distal junction 70a formed between the distal extremity 61 of the inflatable balloon 28 and the distal extremity 64 of the distal inner member 148 includes perforations 241. The perforations 241 may be formed using a laser or mechanical punch, as is known in the art to process catheter material. The perforations 241, may be formed on the distal shaft 118 of the balloon 28 prior to forming the distal seal 67, (fusion or adhesion bonded), to form the distal junction 70a.

Figure 13C:
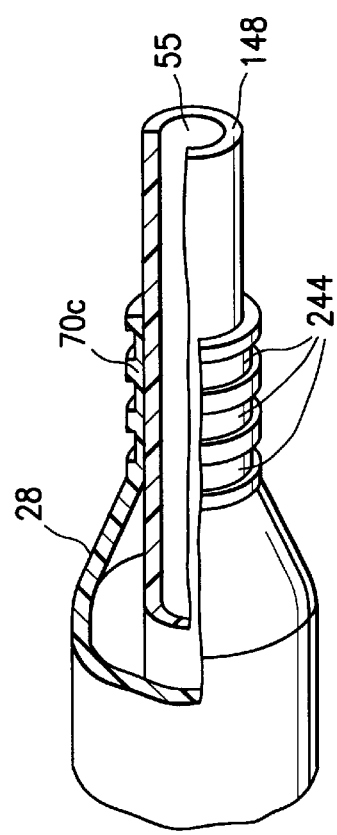
Figure 13B:
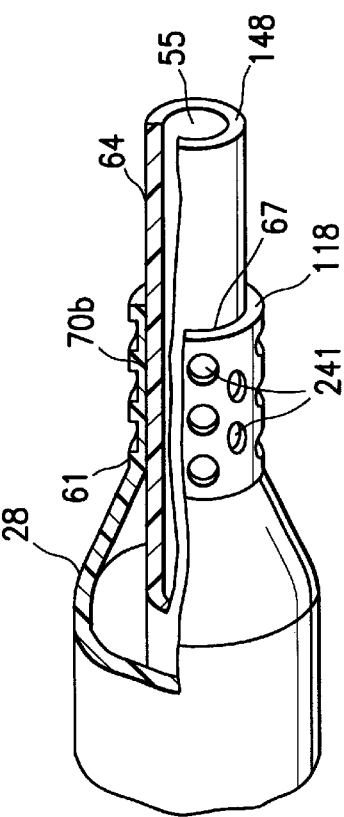

Alternatively, as illustrated in FIG. 13(B) and 13(C), the perforations 241 at the distal junction 70b (FIG. 13(B)) or the grooves 244 at the distal junction 70c (FIG. 13(C)) may be formed after the distal seal 67 has been formed between the distal extremity 61 of the balloon 28 and the distal extremity 64 of the distal inner member 148;

The distal perforations 241 and grooves 244 may or may not extend through to the inner member lumen 55 of the distal inner member 148.

Figure 14:
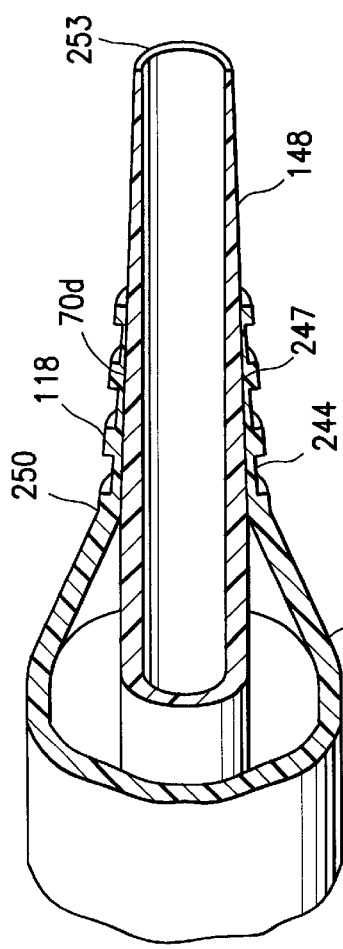
FIG. 14 is cross sectional view, in part, of alternative embodiment of the delivery system of FIGS. 13(A) through 13(C) showing a tapered distal seal.

In another embodiment illustrated in FIG. 14, the distal junction 70d may include a taper 247, with or without the perforations 241 (such as those in FIG. 13(B)) and grooves 244 (as illustrated in FIG. 14, the distal junction 70d includes grooves 244). The tapered distal junction 70d, decreases in diameter from a proximal end 250 of the distal balloon shaft 118 to a point along the distal junction 70d and may extend distally to a distal end 253 of the distal inner member 148. The taper 247 can be applied after the sealing process using methods such as a heated mold. The perforations 241, grooves 244, and the tapered distal junction 70d improve the flexibility transition of the catheter and may be used individually or in combination with one another.

Figure 15A:
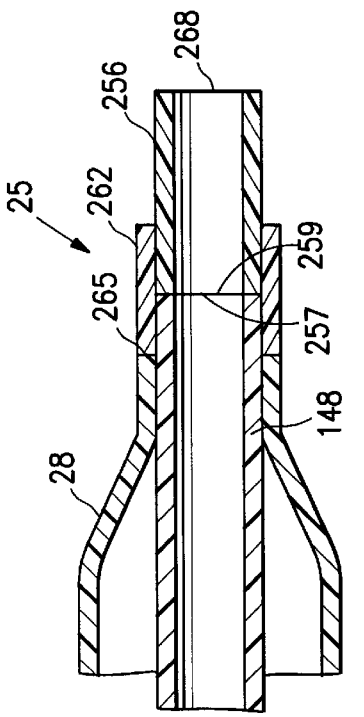
FIG. 15(A) is a cross sectional view, in part, of alternative embodiment of a delivery system having a catheter tip including an atraumatic tip and outer layer member.

In another preferred embodiment illustrated in FIG. 15(A), the catheter tip 25, further includes an atraumatic distal tip 256 formed of suitable material such as those having a flexural modulus ranging from about 1.3 to about $1.7 \times 10^4$ lb/in$^2$ such as PEBAX 40D. The atraumatic distal tip 256 is, preferably, butt-joined at a proximal end 257 to a distal end 259 of the distal inner member 148. Additionally, an outer sleeve 262 formed of flexible material such as PEBAX 55D or 63D may also be butt-joined to a distal end 265 of the balloon 28 at a point proximal to the distal end 259 of the inner tubular member 148 and extends distally to a point proximal to a distal end 268 of the atraumatic distal tip 256. FIG. 15(B) illustrates the catheter tip of FIG. 15(A) after the members have been heat sealed, having a preferred tapered profile.

The presence of the atraumatic distal tip 256 and the optional outer sleeve 262, provide for a smoother decrease in the bending stiffness of the catheter tip 25 in the distal direction.

Figure 15C:
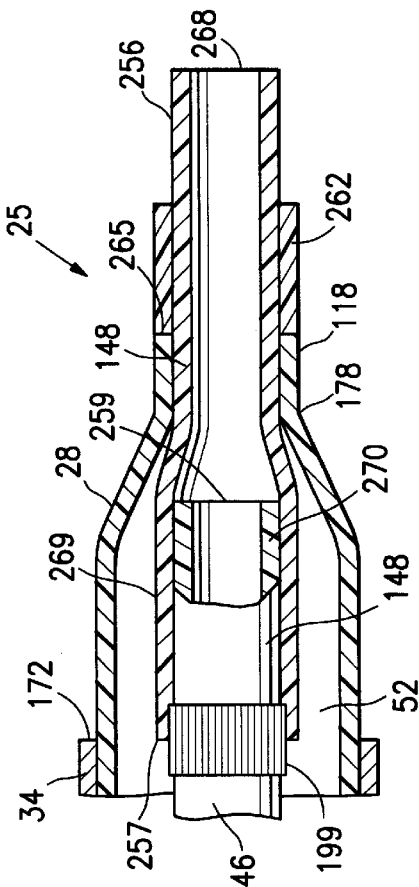
FIG. 15(B) is cross sectional view, in part, of the catheter tip of FIG. 15(A) after a sealing process, the tip being tapered.
Figure 15B:
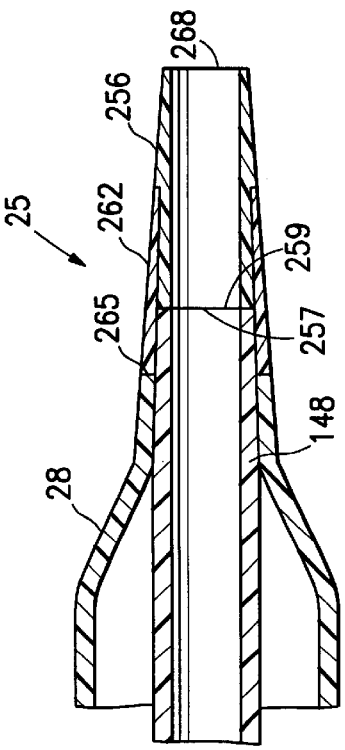

In another embodiment, features of which are illustrated in FIG. 15(C), the distal end 259 of the distal inner member 148 terminates proximal to the proximal end 178 of the distal balloon shaft 118. Preferably, a proximal section 269 of the atraumatic tip 256 extends proximally within the balloon interior chamber 52 overlaying a distal portion 270 of the distal inner member 148. More preferably, the atraumatic tip proximal end 257 extends up to the distal end of the distal marker 199 when present; most preferably, overlaying the distal marker 199.

Figure 16:
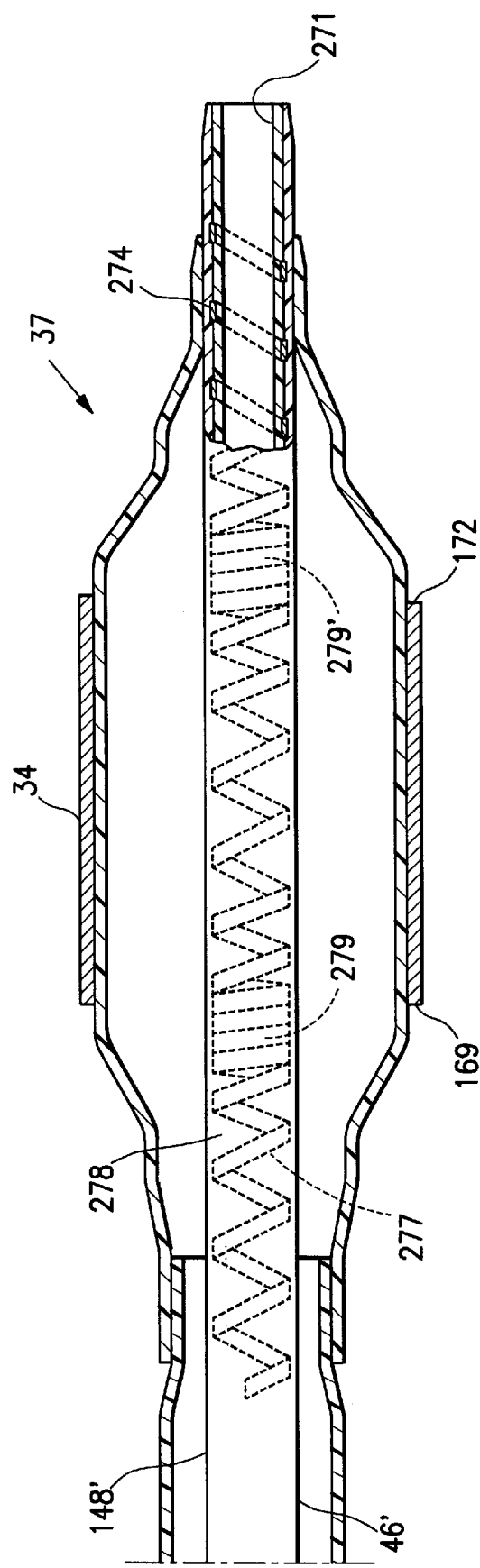
FIG. 16 is a longitudinal cross sectional view, in part, of an alternative embodiment of a delivery system having an inner tubular member comprising at least in part of a tubular member with an imbedded coil, the inner tubular member having variable stiffness along its length.

In one embodiment illustrated in FIG. 16, an inner member 46' comprises, at least in its distal section 148', a tubular member 271 with an imbedded coil 274 for providing a gradual change in stiffness profile of the catheter near and at the stent region. The coil 274 may have variable pitch 277 along its length. As can be seen in FIG. 16, the coil 274 may have a relatively open pitch at a first point 278 near the balloon proximal end, the pitch 277 becoming tighter in the distal direction toward the proximal edge 169 of the stent 34 (when a stent is mounted on the catheter), with a tight pitch 279 near or at the stent proximal edge 169. The pitch 277, becomes more open as the coil 274 moves distally away from the proximal edge 169 of the stent, and becoming tighter at a second tight pitch point 279' near or at the distal edge 172 of the stent 34. The pitch again opens as the coil 274 moves distally away from the distal edge 172 of the stent 34. The tubular member 271 or the coil 274 may be formed of radiopaque material in the appropriate areas, such as tight pitch points 279 and 279' near the ends of the stent, thereby acting as a marker.

Figure 17:
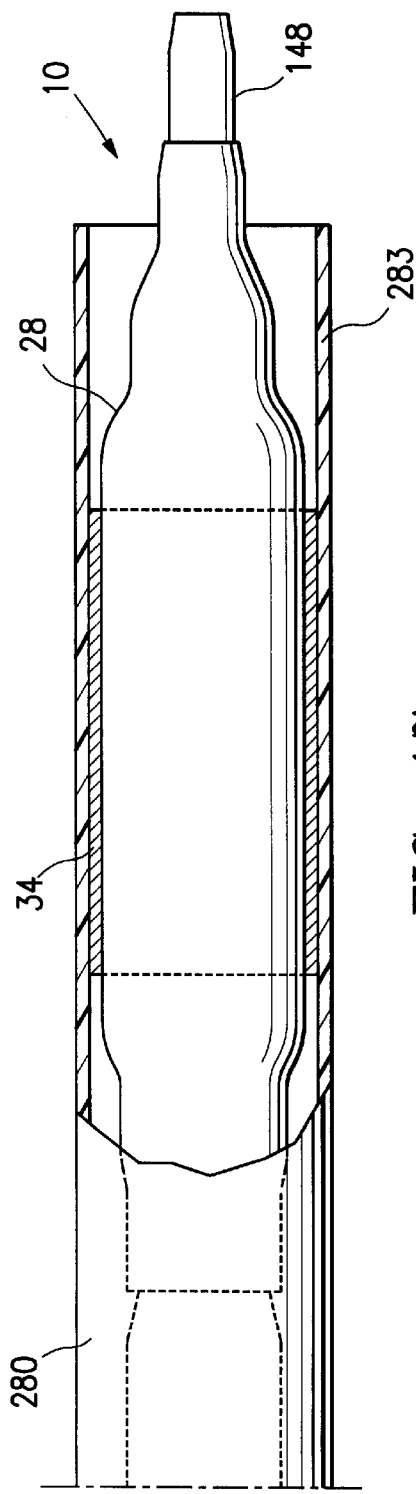
FIG. 17 is longitudinal cross sectional view, in part, of an alternative embodiment of a delivery system having a variable stiffness sheath disposed over at least a part of the stent.
Figure 18:
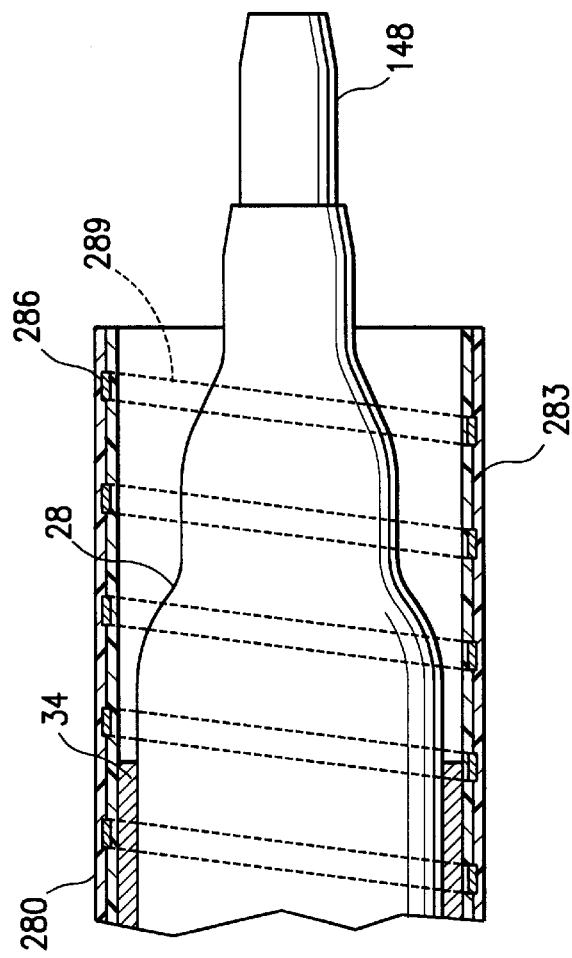
FIG. 18 is a cross section view of an alternative embodiment of the sheath in FIG. 17 having an imbedded coil.

In another embodiment illustrated in FIG. 17, at least a portion of the catheter 10, includes a sheath 280 disposed over, at least part of, the stent 34, the sheath 280 being retractable prior the deployment of the stent 34 in the desired area. The sheath 280 may be selectively stiffened by various means to minimize kink points near or at the ends of the stent 34. The variable stiffness of the sheath 280 may be achieved by, varying a wall thickness 283 of the sheath, varying the material from which the sheath 280 is formed, including an imbedded coil 286 with different pitch 289 along its length as shown in FIG. 18, or varying the outer diameter of the sheath 280.

The stent deploying balloon 28 of the invention can be produced by conventional techniques for producing catheter inflatable members. In a presently preferred embodiment, the balloon is formed within a mold having the general shape of the expanded balloon illustrated in FIG. 4. An extruded polymeric tube is radially expanded and axially expanded within the mold, at elevated temperatures, and may be heat treated one or more times as is conventionally known as, for example, to reduce shrinkage of the balloon. The balloon is secured to the catheter shaft, and is typically folded thereon into a low profile configuration for insertion and advancement within the body lumen of the patient.

The presently preferred balloon material is a polyamide such as polyether block amide, such as those available under the trade designation of PEBAX, such as PEBAX 70D or 63D. However, other suitable materials may be used including polyamide copolymers such as Nylon 12, polyethylenes, and polyurethanes such as PELLETHANE (a polyurethane copolymer). The balloon material may be cross-linked or not, depending upon the nature of the material and characteristics required for a particular application. The presently preferred PEBAX balloon material is not cross-linked. By cross-linking the balloon compliant material, the final inflated balloon size can be controlled. Conventional cross-linking techniques can be used including thermal treatment and E-beam exposure. After cross-linking, initial pressurization, expansion, and preshrinking, the balloon will thereafter expand in a controlled manner to a reproducible diameter in response to a given inflation pressure, and thereby avoid over-expanding the stent to an undesirably large diameter.

The length of the compliant balloon 28 may be from about 0.5 cm to about 6 cm, preferably from about 1.0 cm to about 4.0 cm. With the balloon folded in a low profile configuration for introduction into and advancement within a patient's vasculature, the outer diameter of the balloon catheter at the stent-receiving portion of the balloon 94 with a stent 34 thereon is about 0.040 to about 0.050 in. In an expanded state, the wall thickness is about 0.0005 to about 0.0010 in. The balloon 28 may be provided in a variety of sizes. The inflated outer diameter of the balloon stent-receiving portion 94 within the deployment pressure is about 2.0 to about 5.0 mm. The inflated outer diameter of the proximal and distal intermediate portions 103 and 106 within the deployment pressure is about 100% of that for the stent-receiving portion 94 within the deployment pressure. In a presently preferred embodiment, the length of the intermediate section 85 ranges from about 9 to about 41 mm; the length of the stent-receiving portion 94 ranges from about 8 to about 40 mm; and the length of the proximal and distal tapered areas ranges from about 2 to about 6 mm. The length of the proximal and distal shafts 115 and 118 in a preferred embodiment ranges from about zero to about 1 mm.

In the embodiment illustrated in FIGS. 4, the balloon 28 is symmetrical and the stent-receiving portion 94 is at a central location on the balloon 28. However, alternative balloon designs may be used for particular applications and anatomies.

The stent 34 may be any of a variety of stent materials and forms designed to be implanted by an expanding member, such as, for example, the MULTI-LINK™ stent, commercially available from Guidant Corporation, and the stents described in U.S. Pat. No. 5,514,154 (Lau et al.) and U.S. Pat. No. 5,443,500 (Sigwart), incorporated herein by reference in their entireties. For example, the stent material may be stainless steel, a NiTi alloy, a Co—Cr-Mo containing alloy such as MP-35N, a plastic material, or various other materials. The stent has a smaller diameter for insertion and advancement into the patient's lumen which may be formed by contracting the stent or by folding at least a portion of the stent into a wrapped configuration. It should be noted that the stent 34 may be self or balloon deployable.

Figure 19:
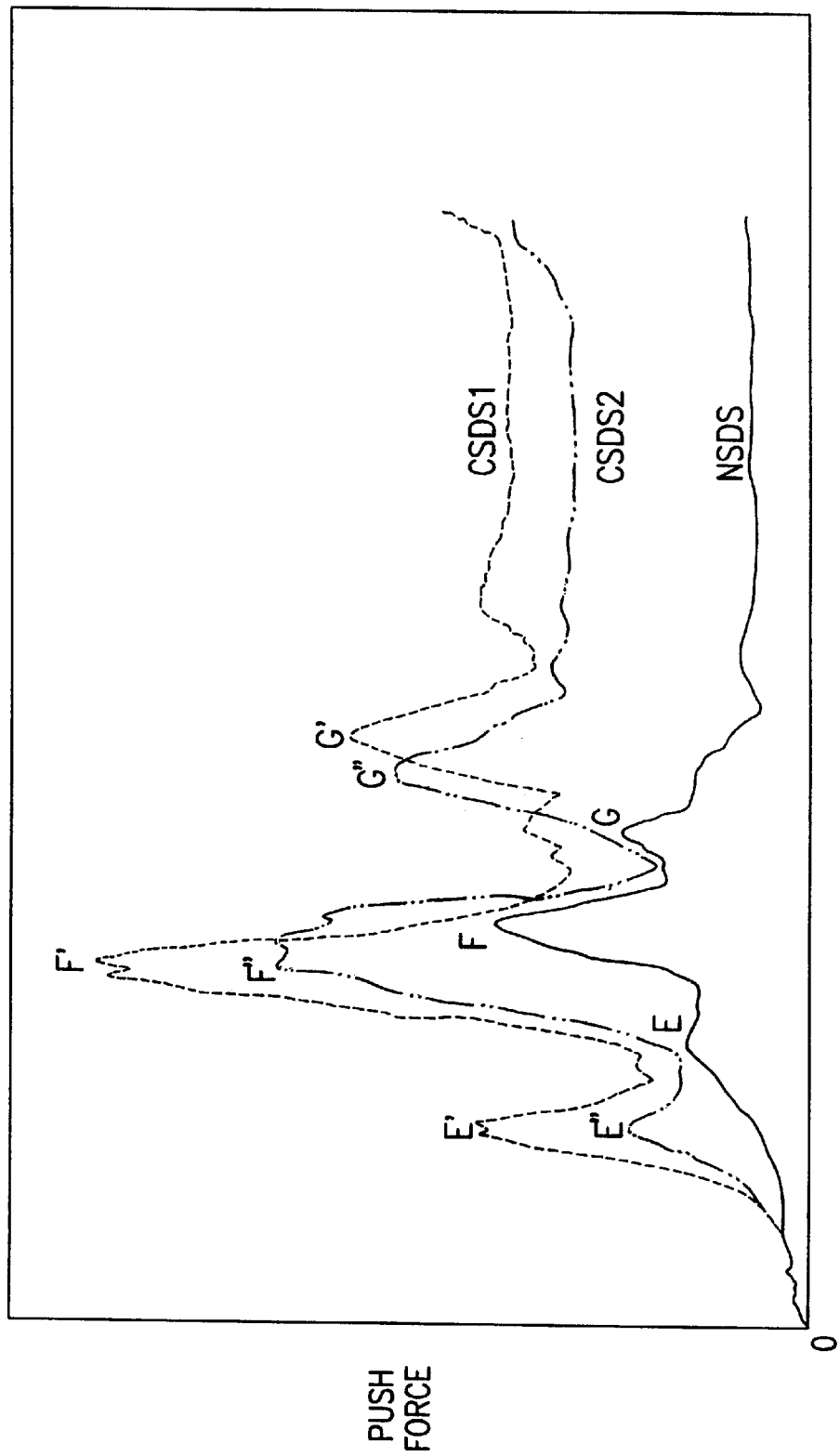
FIG. 19 is a diagrammatic illustration of a force versus distance curve showing a smoother stiffness transition along the catheter of the present invention compared to others.

By way of example, and not as a limitation, the following example is offered:

The optimization of bending stiffness and kink resistance can be observed in a force-displacement graph of a test performed with a neurovascular stent delivery system, NSDS, embodying some of the features of the present invention, and two commercially available coronary stent delivery systems, CSDS 1 AND CSDS 2. The catheters were pushed through a tight radius (e.g., a radius of curvature of about 5 mm with an angle of curve of about 90°) vascular model at a constant rate of speed. A force transducer measured the resistance force of the catheter passing through the model. The applied force through the entire catheter was then plotted against the distance the catheter was advanced through the model, as illustrated in FIG. 19.

Crossing force is a function of, among other things, surface friction and bending stiffness. The various peaks on the graph of FIG. 19, occur when stiff, rigid sections of the catheter device are attempting to pass through the radius of the model. The height of the peak is determined in part by the stiffness and length of the rigid section, and the presence of a kink just distal to the rigid section. For this experiment, the lengths of the different catheter portions among the different catheters did not vary, with the exception of the catheter of the present invention including the atraumatic distal tip and the outer layer member. As can be seen in FIG. 19, three main peaks can generally be observed along each plot. Moving from left to right on the plots, the first (E, E', E"), second (F, F', F"), and the third (G, G', G") peaks correspond to a point along the catheter, respectively, at or about the distal balloon seal, at the stent area, and at or about the proximal balloon seal, with the designations E, E', and E"; F, F', B"; G, C', G" corresponding, respectively, to: NSDS of the present invention;

CSDS 1 available from Guidant Corporation under the trade designation ACS Multi-Link OTW Duet™ Coronary Stent System;

CSDS 2 available from Guidant Corporation under the trade designation ACS Multi-Link OTW Tristar™ Coronary Stent System.

The effect of the marker bands on the two commercial catheters may not be as observable due to the relatively stiffer catheters. Although very stiff, the length of the marker band is relatively short and compared to the relatively stiffer coronary catheters the kink points are not as discernable. On the softer neuro stent delivery system of the present invention, the kink points along the catheter at a location corresponding to the marker bands can be improved utilizing other embodiments described above, such as crimping the stent on the marker bands and adding the jackets to the inner member.

When reviewing FIG. 19, it should be noted, that although the crossing force profile is dependent on the bending stiffness, it is also a function of other parameters such as, surface friction and length of rigid sections.

As can further be observed from FIG. 19, at all stages of the catheter, the magnitude of force required to push the coronary devices, as well as the amplitude, is much greater than the same for the neuro stent delivery system of the present invention. Furthermore, the slope (i.e., transition between points of differing stiffness along the catheter) of the curves leading to the peaks and valleys are less severe for the catheter of the present invention.

While particular forms of the invention have been illustrated and described, it will be apparent that various modifications can be made without departing from the spirit and scope of the invention. Accordingly, it is not intended that the invention be limited, except as by the appended claims.

What is claims is:

1. A stent delivery system, comprising:
   a catheter having an elongated shaft with proximal and distal ends and an inner lumen extending therein, the catheter having more than one portion with different stiffness values, each portion comprising components that gradually transition the stiffness of that portion to an adjacent portion;
   an enlargeable member mounted on a distal shaft section proximal to the distal end which is configured for supporting a deployable prosthetic device on a receiving portion thereon, which has an interior in fluid communication with the inner lumen; and
   the shaft including a tubular member extending through the interior of the enlargeable member, and including at least one portion which is stiffer than a portion immediately proximal to the at least one portion of the shaft, wherein the immediately proximal portion of the shaft includes components that gradually transition the stiffness of the immediately proximal portion to the at least one portion of the shaft.

2. The system of claim 1 wherein enlargable member has proximal and distal ends, and wherein the more than one portion having different stiffness values is disposed longitudinally along a first section of the catheter between first and second points, the first and second points having the same transverse location as the enlargable member proximal end and distal ends, respectively, each portion comprising of components that gradually match the stiffness of that portion to an adjacent portion.

3. The system of claim 1 wherein the stiffness ratio between any two adjacent portions is at least 0.3.

4. The system of claim 3 wherein the stiffness ratio between any two adjacent portions is between 0.3 and 0.7.

5. The system of claim 4 wherein the stiffness between any two adjacent portions along the first section is at least 0.7.

6. The system of claim 1 wherein the catheter shaft comprises an outer tubular member and an inner tubular member, the outer tubular member including more than one section, the sections having a decrease in stiffness in the distal direction.

7. The system of claim 6 wherein the outer tubular member includes a proximal, an intermediate, and a distal outer member, the members having a lower stiffness value than the section immediately proximal thereto.

8. The system of claim 7 wherein the proximal outer tubular member is formed of a material having a flexural modulus in a range from about $50 \times 10^4$ to about $200 \times 10^4$ lb/in$^2$.

9. The system of claim 7 wherein the proximal outer tubular member is formed of a material selected from the group consisting of polyetheretherketone, polyetherimide, and stainless steel.

10. The system of claim 9 wherein the proximal outer tubular member is formed of polyetheretherketone.

11. The system of claim 7 wherein the intermediate outer tubular member is formed of a material having a flexural modulus in a range from about $5 \times 10^4$ to about $6 \times 10^4$ lb/in$^2$.

12. The system of claim 7 wherein the intermediate outer tubular member is formed of polyether block amide with a Shore D hardness of about 60 to about 70.

13. The system of claim 12 wherein the intermediate outer tubular member is formed of polyether block amide with a Shore D hardness of about 63.

14. The system of claim 12 wherein the distal outer tubular member is formed of a material having a stiffness value in a range from about $1.3 \times 10^4$ to about $1.7 \times 10^4$ lb/in$^2$.

15. The system of claim 7 wherein the distal outer tubular member is formed of polyether block amide with a Shore D hardness of about 40.

16. The system of claim 6 wherein the inner tubular member includes proximal and distal inner tubular members, the distal inner tubular member having a lower stiffness value than the proximal inner tubular member.

17. The system of claim 16 wherein the proximal inner tubular member is formed of a material having a flexural modulus in a range from about $50 \times 10^4$ to about $200 \times 10^4$ lb/in$^2$.

18. The system of claim 16 wherein the proximal inner tubular member is formed of polyetheretherketone.

19. The system of claim 16 wherein the distal inner tubular member is formed of a material having a flexural modulus in a range from about $1.3 \times 10^4$ to about $5 \times 10^4$ lb/in$^2$.

20. The system of claim 16 wherein the distal inner tubular member is formed of a co-extrusion material comprising polyether block amide with a Shore D hardness of about 40 and high density polyethylene.

21. The system of claim 1 further including proximal and distal radiopaque markers disposed on a portion of the tubular member extending within the interior of the enlargable member.

22. The system of claim 21 wherein a portion of each marker being within and a portion being outside the receiving portion of the enlargable member.

23. The system of claim 1 further including a deployable member disposed on the enlargable member receiving portion.

24. The system of claim 23 further including a retractable sheath disposed over at least a portion of the catheter shaft including the deployable member.

25. The system of claim 24 wherein the sheath has a variable stiffness to minimize kinking of the catheter near or at proximal and distal ends of the deployable member.

26. The system of claim 1 wherein the tubular member extending within the interior of the enlargeable member includes an embedded coiled member along at least a first portion located adjacent to a second portion of the tubular member extending along the receiving portion of the enlargeable member, the coiled member increasing the stiffness of the tubular member first portion relative to the tubular member second portion to thereby provide a gradual transition in stiffness to the enlargeable member receiving portion upon receiving the deployable member thereon.

27. The system of claim 26 wherein the tubular member first portion is adjacent to a proximal end of the second portion, and the tubular member has a third portion adjacent to a distal end of the second portion, and the coiled member extends along at least the first, second, and third portions of the tubular member, and the coiled member has a varying pitch which is more open along the tubular member second portion than along the first and third portions adjacent thereto, so that the tubular member has a stiffness along the receiving portion of the enlargeable member which is less than the stiffness of the tubular member adjacent thereto at either end of the receiving portion.

28. The system of claim 27 wherein the coiled member extends along a forth portion located proximally adjacent to the first portion of the tubular member, and the coiled member pitch is more open along the tubular member forth portion than along the first portion of the tubular member.

29. A stent delivery system, comprising:

a catheter having an elongated shaft with proximal and distal ends and an inner lumen extending therein, the catheter having more than one portion with different stiffness values, each portion comprising components that gradually transition the stiffness of that portion to an adjacent portion;

an enlargeable member mounted on a distal shaft section proximal to the distal end of the shaft, which is configured for supporting a deployable prosthetic device on a receiving portion thereon, and which has a proximal end, a distal end, and an interior in fluid communication with the inner lumen; and the shaft including a tubular member extending through the interior of the enlargeable member, and wherein the more than one portions having different stiffness values are disposed longitudinally along a first section of the catheter between the first and second points, the first and second points having the same transverse location as the enlargeable member proximal end and distal ends, respectively.

30. A stent delivery system, comprising:

a catheter having an elongated shaft with proximal and distal ends and an inner lumen extending therein, the catheter having more than one portion with different stiffness values, each portion comprising of components that gradually transition the stiffness of that portion to an adjacent portion, wherein the stiffness ratio between any two adjacent portions is at least 0.3;

an enlargeable member mounted on a distal shaft section proximal to the distal end which is configured for supporting a deployable prosthetic device on a receiving portion thereon, which has an interior in fluid communication with the inner lumen; and the shaft including a tubular member extending through the interior of the enlargeable member.

31. A stent delivery system, comprising:

a catheter having an elongated shaft with proximal and distal ends and an inner lumen extending therein, the catheter shaft having an outer tubular member and an inner tubular member, the outer tubular member has multiple sections having a decrease in stiffness in the distal direction, the sections comprising a proximal, an intermediate, and a distal outer member, the proximal, intermediate, and distal outer members have a lower stiffness value than the section immediately proximal thereto, so that the catheter has more than one portion with different stiffness values, each portion comprising components that gradually transition the stiffness of that portion to an adjacent portion;

an enlargeable member mounted on a distal shaft section proximal to the distal end which is configured for supporting a deployable prosthetic device on a receiving portion thereon, which has an interior in fluid communication with the inner lumen; and the shaft inner tubular member extends through the interior of the enlargeable member.

32. The system of claim 31 wherein the inner tubular member has multiple sections having a decrease in stiffness in the distal direction, the sections comprising a proximal inner member and a distal inner member, and the proximal inner member is joined to the distal inner member at a junction located proximal to the distal outer tubular member.

33. A stent delivery system, comprising:

a catheter having an elongated shaft with proximal and distal ends and an inner lumen extending therein, the catheter having more than one portion with different stiffness values, each portion comprising of components that gradually transition the stiffness of that portion to an adjacent portion;

an enlargeable member mounted on a distal shaft section proximal to the distal end which is configured for supporting a deployable prosthetic device on a receiving portion thereon, which has an interior in fluid communication with the inner lumen;

the shaft including a tubular member extending through the interior of the enlargeable member;

a deployable member disposed on the enlargeable member receiving portion; and a retractable sheath which is disposed over at least a portion of the catheter shaft including the deployable member, and which has a variable stiffness to minimize kinking of the catheter near or at proximal and distal ends of the deployable member.

* * * * *